(12) United States Patent
Gopal

(10) Patent No.: US 8,058,022 B2
(45) Date of Patent: Nov. 15, 2011

(54) DIAGNOSIS AND MONITORING OF MYCOBACTERIUM TUBERCULOSIS INFECTION

(75) Inventor: Balsubramanian Gopal, Bangalore (IN)

(73) Assignee: Indian Institute of Science, Karnataka (IN)

( * ) Notice: Subject to any disclaimer, the term of this patent is extended or adjusted under 35 U.S.C. 154(b) by 0 days.

(21) Appl. No.: 12/560,904

(22) Filed: Sep. 16, 2009

(65) Prior Publication Data
US 2011/0021367 A1 Jan. 27, 2011

(30) Foreign Application Priority Data
Jul. 27, 2009 (IN) .......................... 1774/CHE/2009

(51) Int. Cl.
| | |
|---|---|
| C12Q 1/00 | (2006.01) |
| G01N 33/53 | (2006.01) |
| G01N 33/554 | (2006.01) |
| G01N 1/30 | (2006.01) |
| G01N 33/543 | (2006.01) |
| G01N 33/549 | (2006.01) |
| C40B 30/04 | (2006.01) |

(52) U.S. Cl. ....... 435/7.32; 436/518; 436/532; 436/536; 436/538; 436/540; 506/9; 435/4; 435/7.1; 435/7.2; 435/40.5; 435/40.51; 435/40.52

(58) Field of Classification Search .................. None
See application file for complete search history.

(56) References Cited

U.S. PATENT DOCUMENTS

| | | | |
|---|---|---|---|
| 5,700,925 | A | 12/1997 | Bishai et al. |
| 5,824,546 | A | 10/1998 | Bishai et al. |
| 6,004,764 | A | 12/1999 | Bishai et al. |
| 6,994,985 | B1 | 2/2006 | Werner et al. |
| 2004/0146933 | A1 | 7/2004 | Quinn et al. |
| 2005/0260663 | A1 | 11/2005 | Solomon |
| 2008/0241182 | A1 | 10/2008 | Jain et al. |

FOREIGN PATENT DOCUMENTS

| | | |
|---|---|---|
| WO | WO 97/35611 | 10/1997 |
| WO | WO-99/64866 | 12/1999 |
| WO | WO-2007/014304 | 2/2007 |

OTHER PUBLICATIONS

Hughes, K. et al., "The Anti-Sigma Factors," Annu. Rev. of Microbiol., 1998, vol. 52, pp. 231-286.
International Search Report and Written Opinion for PCT/IB2010/001801 mailed Nov. 18, 2010.
Li, W. et al., "Identification and Structure of the Anti-sigma Factor binding Domain of the Disulphide-stress Regulated Sigma Factor $\sigma^R$ from *Streptomyces coelicolor*," J. Mol. Biol., 2002, vol. 323, pp. 225-236.
Malik, S. et al., "Interactions of the M. *tuberculosis* UsfX with the cognate sigma factor SigF and the anti-anti sigma factor RsfA," Biochimica Et Biophysica Acta, 2009, vol. 1794, pp. 541-553.
Thakur, K. et al., "Structural and Biochemical Bases for the Redox Sensitivity of *Mycobacterium tuberculosis* RsIA," J. Mol. Biol., 2010, vol. 397, pp. 1199-1208.
Arnvig, K. B. et al., "A high-affinity interaction between NusA and the *rrn nut* site in *Mycobacterium tuberculosis*," PNAS, vol. 101, No. 22, Jun. 1, 2004, pp. 8325-8330.
Arnvig, K. B. et al., "The mechanism of upstream activation in the *rrnB* operon of *Mycobacterium smegmatis* is different from the *Escherichia coli* paradigm," Microbiology, vol. 151, 2005, pp. 467-473.
Collins, D. M. et al., "Mutation of the principal σ factor causes loss of virulence in a strain of the *Mycobacterium tuberculosis* complex," Proc. Natl. Acad. Sci., vol. 92, Aug. 1995, pp. 8036-8040.
Covert, M. W. et al., "Transcriptional Regulation in Constraints-based Metabolic Models of *Escherichia coli*," The Journal of Biological Chemistry, vol. 277, No. 31, Aug. 2, 2002, pp. 28058-28064.
Dainese, E. et al, "Posttranslational Regulation of *Mycobacterium tuberculosis* Extracytoplasmic-Function Sigma Factor $\sigma^L$ and Roles in Virulence and in Global Regulation of Gene Expression," Infection and Immunity, vol. 74, No. 4, Apr. 2006, pp. 2457-2461.
Dona, V. et al., "Evidence of Complex Transcriptional, Translational, and Posttranslational Regulation of the Extracytoplasmic Function Sigma Factor $\sigma^E$ in *Mycobacterium tuberculosis*," Journal of Bacteriology, vol. 190, No. 17, Sep. 2008, pp. 5963-5971.
Fleischmann, R.D. et al., "Whole-Genome Comparison of *Mycobacterium tuberculosis* Clinical and Laboratory Strains," Journal of Bacteriology, vol. 184, No. 19, Oct. 2002, pp. 5479-5490.
Manganelli, R. et al., "The Extra Cytoplasmic Function Sigma Factor $\sigma^E$ Is Essential for *Mycobacterium tuberculosis* Virulence in Mice," Infection and Immunity, vol. 72, No. 5, May 2004, pp. 3038-3041.
Manganelli, R. et al., "σ Factors and Global Gene Regulation in *Mycobacterium tuberculosis*,"Journal of Bacteriology, vol. 186, No. 4, Feb. 2004, pp. 895-902.
Thakur, K. G. et al., "Crystallization and preliminary X-ray diffraction studies of two domains of a bibbed extra-cytoplasmic function sigma factor SigC from *Mycobacterium tuberculosis*," ACTA CRYST., vol. F61, 2005, pp. 779-781.
Thakur, K. G. et al., Structural and Biophysical Studies on Two Promoter Recognition Domains of the Extra-cytoplasmic Function $\sigma^C$ Factor from *Mycobacterium tuberculosis*, Journal of Biological Chemistry, vol. 282, No. 7, Feb. 16, 2007, pp. 4711-4718.

*Primary Examiner* — Oluwatosin Ogunbiyi
(74) *Attorney, Agent, or Firm* — Foley & Lardner LLP

(57) ABSTRACT

Disclosed are methods for detecting protein complexes of sigma factors and interacting proteins in a sample containing *Mycobacterium tuberculosis*. Such methods are useful for the diagnosis and/or monitoring of tuberculosis in a subject. Also disclosed are methods for screening compounds that affect the interaction of one or more sigma factors with one or more interacting proteins.

14 Claims, 7 Drawing Sheets

A.

B.

A.

B.

DIAGNOSIS AND MONITORING OF MYCOBACTERIUM TUBERCULOSIS INFECTION

CROSS-REFERENCE TO RELATED APPLICATIONS

This application claims priority to Indian Patent Application No. 1774/CHE/2009, filed Jul. 27, 2009, the entire contents of which are hereby incorporated by reference in its entirety.

TECHNICAL FIELD

The present technology relates generally to the fields of molecular biology and pharmacology and to the diagnosis, prognosis or prevention/therapeutic treatment of tuberculosis. The technology further relates to screening methods for identifying compounds that inhibit or alter the growth of *Mycobacterium tuberculosis*.

BACKGROUND

*Mycobacterium tuberculosis* is the bacillus which causes tuberculosis in humans. Tuberculosis affects about 2 billion people—about one third of the world's population, according to WHO estimates. This bacillus can lie latent within the host, often for several decades, until the disease gets triggered. A mycobacterial infection often manifests itself when the carrier is immunocompromised, either by nutritional deficiency or the acquired immunodeficiency syndrome (AIDS). The transcriptional machinery is of particular importance in this organism as it has only one ribosomal RNA operon, making efficient transcription necessary for the survival and pathogenicity of this organism. This aspect makes the transcription machinery an attractive target for drug-design. Indeed, a key component of tuberculosis therapy is rifampicin, an RNA polymerase inhibitor.

The central enzyme of bacterial gene expression, the DNA-dependent RNA polymerase, consists of five sub-units. The two $\alpha$ subunits along with the $\beta$ and $\beta'$ subunits form a stable catalytic unit that is involved in RNA elongation. The fifth subunit of RNA polymerase is the sigma factor ($\sigma$) that provides the RNA polymerase with promoter recognition features and is necessary for the initiation of transcription. *M. tuberculosis* has at least 13 sigma ($\sigma$) factors: 3 primary sigma factors, 10 extra-cytoplasmic function (ECF) sigma factors and one alternative sigma factor, pvdS. The interplay between signal transduction and the transcriptional regulatory mechanisms allows the bacillus to respond to changes in the environment by synthesizing new proteins or down-regulating others. This ability is key to the bacillus's adaptability to survive the stresses inside the host until a failure in host defenses leads to a reactivation of the disease.

SUMMARY

This technology relates generally to analytical testing of samples, and to aspects of biomarker elucidation for the diagnosis, prognosis, or prevention/therapeutic treatment of tuberculosis. In one aspect, the disclosure provides a method for diagnosing or monitoring tuberculosis in a subject comprising: (a) detecting in a sample from the subject whether one or more sigma factors of *Mycobacterium tuberculosis* are bound to one or more interacting proteins; and (b) determining a pattern of interaction between the one or more sigma factors and the one or more interacting proteins in the sample, wherein the pattern of interaction indicates the presence or status of tuberculosis in the subject. In various embodiments, the status of tuberculosis is active tuberculosis, latent infection or recent infection.

In an illustrative embodiment, the detecting is by contacting the sample with a solid support conjugated to one or more binding agents having specific binding sites for the one or more sigma factors and identifying the one or more interacting proteins bound to the one or more sigma factors. In one embodiment, the solid support has the one or more binding agents immobilized at discrete locations. In one embodiment, the solid support is an antibody array.

In an illustrative embodiment, identifying the one or more interacting proteins bound to the one or more sigma factors is by contacting the sample with one or more labeled binding agents specific for the one or more interacting proteins. In one embodiment, the one or more binding agents are antibodies that have been raised against one or more sigma factors from *Mycobacterium tuberculosis*. The antibodies may be polyclonal antibodies or monoclonal antibodies.

In an illustrative embodiment, the detecting is by contacting the sample with a solid support conjugated to recombinant sigma factor proteins and identifying the one or more interacting proteins bound to the one or more recombinant sigma factor proteins. In one embodiment, the solid support is an array of recombinant sigma factor proteins.

In an illustrative embodiment, the detecting is by immunoprecipitating the one or more sigma factors in the sample and identifying the one or more interacting proteins bound to the one or more sigma factors.

In one embodiment, the one or more sigma factors are selected from the group consisting of: $\sigma^A, \sigma^B, \sigma^C, \sigma^D, \sigma^E, \sigma^F, \sigma^G, \sigma^H, \sigma^I, \sigma^J, \sigma^K, \sigma^L, \sigma^M$, and pvdS. In one embodiment, the one or more interacting proteins are anti-sigma factors.

In one embodiment, the sample is a fluid or tissue sample containing *Mycobacterium tuberculosis*. In one embodiment, the sample is from an isolated culture of *Mycobacterium tuberculosis* from a sample previously obtained from the subject. In one embodiment, the sample is a protein extract from a fluid or tissue sample containing *Mycobacterium tuberculosis*.

In one embodiment, the pattern of interaction indicates that the subject is a candidate for treatment with one or more drugs selected from the group consisting of: isoniazid, streptomycin sulfate, di-hydro-streptomycin, rifampin, pyrazinamide, ethambutol, etionamide, capreomycin sulfate, amikacin, kanamycin sulfate, levofloxacin, p-aminosalicylic acid, D-cycloserine, and clofazimine.

In one aspect, the disclosure provides a method for generating a network of interaction partners of one or more sigma factors of *Mycobacterium tuberculosis* comprising: (a) exposing a culture of *Mycobacterium tuberculosis* to a defined set of conditions; (b) detecting whether the one or more sigma factors are bound to one or more interacting proteins; and (c) determining a pattern of interaction between the one or more sigma factors and the one or more interacting proteins in said sample, thereby providing a network of interaction partners of one or more sigma factors of *Mycobacterium tuberculosis*.

In one embodiment, the one or more sigma factors are selected from the group consisting of: $\sigma^A, \sigma^B, \sigma^C, \sigma^D, \sigma^E, \sigma^F, \sigma^G, \sigma^H, \sigma^I, \sigma^J, \sigma^K, \sigma^L, \sigma^M$, and pvdS. In one embodiment, the one or more interacting proteins are anti-sigma factors.

In one embodiment, the defined set of experimental conditions are selected from the group consisting of: oxidative stress, carbon starvation, nitrosative stress, exposure to antibiotics, and growth in biofilms.

In another aspect, the disclosure provides a method for identifying an agent that inhibits or alters gene transcription in *Mycobacterium tuberculosis* comprising: (a) exposing a culture of *Mycobacterium tuberculosis* to an agent; (b) determining a pattern of interaction between the one or more sigma factors and the one or more interacting proteins in a sample from the culture; and (c) comparing the pattern of interaction to a control pattern to determine whether the compound inhibits or alters gene transcription in *Mycobacterium tuberculosis*. In some embodiments, the agent may be one or more of a protein, a peptide, an aptamer or a small molecule compound.

In another aspect, the disclosure provides a method for identifying targets for compounds which inhibit the growth of *Mycobacterium tuberculosis* comprising: (a) identifying the interaction of one or more *Mycobacterium tuberculosis* sigma factors from a samples of *Mycobacterium tuberculosis* under two or more environmental conditions; (b) identifying the pattern of environment-related protein transcription from the samples; (c) creating a map of the organism's transcription by integrating information obtained in (a) and (b); and (d) identifying drug targets by comparing differences between the interaction of the one or more *Mycobacterium tuberculosis* sigma factors under the two or more environmental conditions.

The foregoing summary is illustrative only and is not intended to be in any way limiting. In addition to the illustrative aspects, embodiments, and features described above, further aspects, embodiments, and features will become apparent by reference to the following drawings and the detailed description.

DETAILED DESCRIPTION

Figure 1:
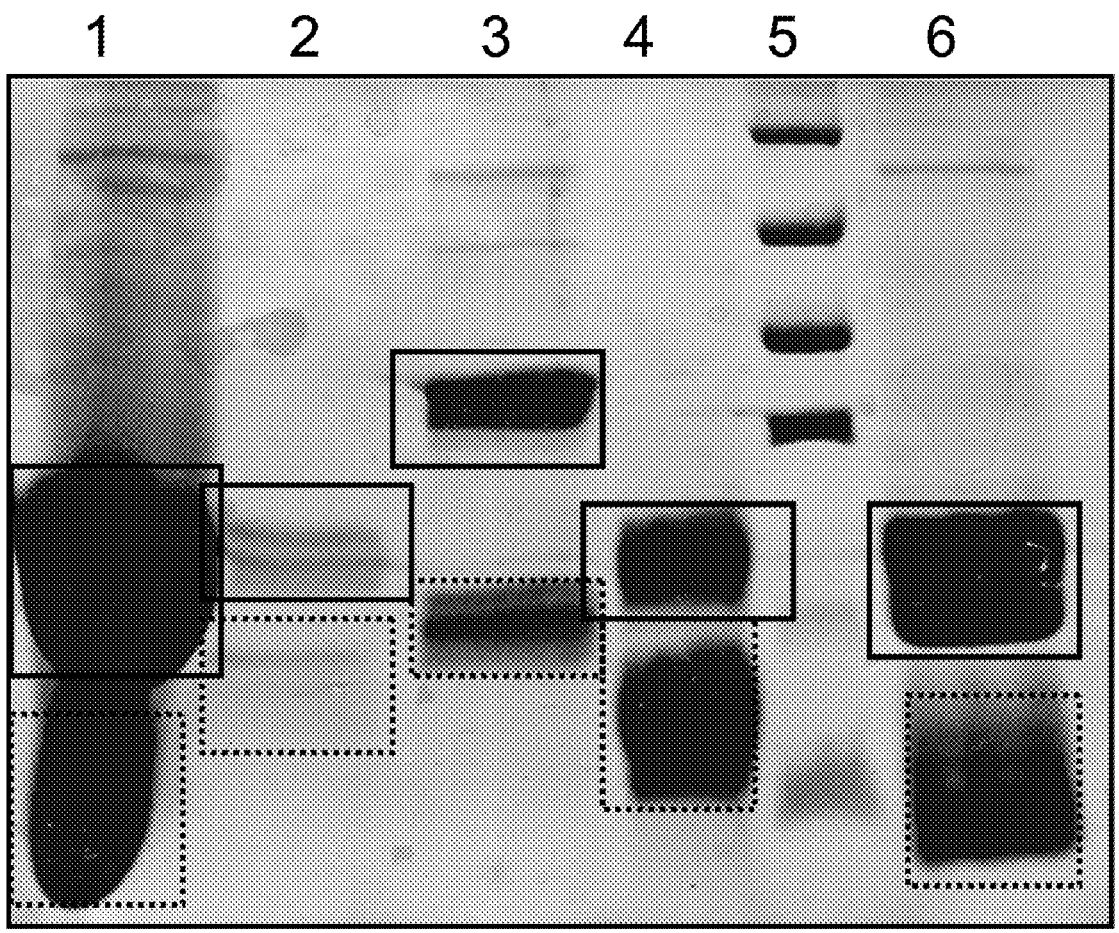
FIG. 1 is a photograph of illustrative embodiments of an SDS-PAGE gel showing complexes of σ factors and anti-σ factor proteins. Lane 1 shows the separation of the $\sigma^D$ and anti-$\sigma^D$ complex; Lane 2 shows the separation of the $\sigma^E$ and Rv1222 complex; Lane 3 shows the separation of the $\sigma^F$ and RsbW complex; Lane 4 shows the separation of the $\sigma^K$ and Rv0444c complex; and Lane 6 corresponds to the $\sigma^L$ and anti $\sigma^L$ pair. Lane 5 is a molecular weight marker.

In the following detailed description, reference may be made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

The present technology is described herein using several definitions, as set forth throughout the specification. As used herein, unless otherwise stated, the singular forms "a," "an," and "the" include plural reference. Thus, for example, a reference to "an oligonucleotide" includes a plurality of oligonucleotide molecules, and a reference to "a protein" is a reference to one or more proteins.

The term "antibody" as used herein encompasses both monoclonal and polyclonal antibodies that fall within any antibody classes, e.g., IgG, IgM, IgA, IgE, or derivatives thereof. The term "antibody" also includes antibody fragments including, but not limited to, Fab, F(ab')$_2$, and conjugates of such fragments, and single-chain antibodies comprising an antigen recognition epitope. In addition, the term "antibody" also means humanized antibodies, including partially or fully humanized antibodies. An antibody may be obtained from an animal, or from a hybridoma cell line producing a monoclonal antibody, or obtained from cells or libraries recombinantly expressing a gene encoding a particular antibody.

The terms "assessing" and "evaluating" are used interchangeably to refer to any form of measurement, and include determining if a characteristic, trait, or feature is present or not. The terms "determining," "measuring," "assessing," and "assaying" are used interchangeably and include both quantitative and qualitative determinations. Assessing may be relative or absolute. "Assessing the presence of" includes determining the amount of something present, as well as determining whether it is present or absent.

As used herein, the term "biomarker" in the context of the present technology refers to a pattern of interaction between the one or more sigma factors and one or more interacting proteins which are differentially present in a test sample as compared to a reference sample, e.g., a control sample.

As used herein, the term "contacting" means bringing into contact so that two or more proteins or peptides can interact with each other, typically under physiological or experimental conditions.

As used herein, the term "diagnosis" means detecting a disease or disorder or determining the stage or degree of a disease or disorder. The term "diagnosis" also encompasses determining the therapeutic effect of a drug therapy, or predicting the pattern of response to a drug therapy. The diagnostic methods may be used independently, or in combination with other diagnosing and/or staging methods known in the medical art for a particular disease or disorder, e.g., tuberculosis.

As used herein, the phrase "difference of the level" refers to differences in the quantity of a particular protein interaction present in a sample as compared to a control. In one embodiment, a biomarker can be an interaction between the one or more sigma factors and one or more interacting proteins. The biomarker may be present at an elevated amount or at a decreased amount in samples of tuberculosis patients compared to a reference level.

In one embodiment, a "difference of a level" may be a difference between the detectable quantity of the particular protein interaction present in a sample as compared to a control of at least about 1%, at least about 2%, at least about 3%, at least about 5%, at least about 10%, at least about 15%, at least about 20%, at least about 25%, at least about 30%, at least about 35%, at least about 40%, at least about 50%, at least about 60%, at least about 75%, at least about 80% or more.

In one embodiment, a "difference of a level" may be a statistically significant difference between the detectable quantity of the particular protein interaction present in a sample as compared to a control. For example, a difference may be statistically significant if the measured level of the particular protein interaction falls outside of about 1.0 standard deviations, about 1.5 standard deviations, about 2.0 standard deviations, or about 2.5 stand deviations of the mean of any control or reference group.

As used herein, the term "effective amount" of a test compound is a quantity sufficient to achieve a desired therapeutic and/or prophylactic effect, for example, an amount which results in the prevention of or a decrease in the symptoms associated with a disease that is being treated, i.e., tuberculosis. The amount of compound administered to the subject will depend on the type and severity of the disease and on the characteristics of the individual, such as general health, age, sex, body weight and tolerance to drugs. It will also depend on the degree, severity or stage of disease. The skilled artisan will be able to determine appropriate dosages depending on these and other factors.

The term "interacting proteins" refers to polypeptides that either directly or indirectly interact via a protein binding interaction with a sigma factor polypeptide. In the latter case, there is no direct contact between the direct interaction partner and the sigma factor protein. Rather, one or more additional proteins form a "bridge" between these interacting protein and the sigma factor. In illustrative embodiments, the interacting proteins include, but are not limited to, other sigma factor proteins, anti-sigma factor proteins and anti-anti-sigma factor proteins.

The terms "interacting" or "binding" refer to a transient or permanent contact between two proteins or polypeptides. An "interaction" between two protein domains, fragments or complete proteins can be determined by a number of methods. For example, an interaction is detectable by any commonly accepted approaches, including functional assays such as the two-hybrid systems. Protein-protein interactions can also be determined by various biophysical and biochemical approaches based on the affinity binding between the two interacting partners. Such biochemical methods generally known in the art include, but are not limited to, protein affinity chromatography, affinity blotting, immunoprecipitation, and the like. The binding constant for two interacting proteins, which reflects the strength or quality of the interaction, can also be determined using methods known in the art.

The term "latent tuberculosis" refers to a stage in the *M. tuberculosis* infection where the bacilli remain viable but are slowly replicating or non-replicating, may be encapsulated in localized lesions within the lung, and/or do not cause active necrotic disease. The latent stage may exist for the remainder of a subject's life, or the infection may reactivate during, for instance, a period of decreased host immunity or in response to other stressors.

The terms "polypeptide," "protein," and "peptide" are used herein interchangeably to refer to amino acid chains in which the amino acid residues are linked by peptide bonds or modified peptide bonds. The amino acid chains can be of any length of greater than two amino acids. Unless otherwise specified, the terms "polypeptide," "protein," and "peptide" also encompass various modified forms thereof. Such modified forms may be naturally occurring modified forms or chemically modified forms. Examples of modified forms include, but are not limited to, glycosylated forms, phosphorylated forms, myristoylated forms, palmitoylated forms, ribosylated forms, acetylated forms, ubiquitinated forms, etc. Modifications also include intra-molecular crosslinking and covalent attachment to various moieties such as lipids, flavin, biotin, polyethylene glycol or derivatives thereof, etc. In addition, modifications may also include cyclization, branching and cross-linking Further, amino acids other than the conventional twenty amino acids encoded by genes may also be included in a polypeptide.

As used herein, the term "protein complex" means a composite unit that is a combination of two or more proteins formed by interaction between the proteins. Typically, but not necessarily, a "protein complex" is formed by the binding of two or more proteins together through specific non-covalent binding affinities. However, covalent bonds may also be present between the interacting partners. For instance, the two interacting partners can be covalently crosslinked so that the protein complex becomes more stable.

As used herein, the term "reference level" refers to an amount or concentration of a biomarker which may be of interest for comparative purposes. In one embodiment, a reference level may be the level of at least one biomarker expressed as an average of the level of the at least one biomarker from samples taken from a control population of healthy subjects. In another embodiment, the reference level may be the level of at least one biomarker in the same subject at an earlier time, i.e., before the present assay. In even another embodiment, the reference level may be the level of at least one biomarker in the subject prior to receiving a treatment regime.

As used herein, the term "sample" may include, but is not limited to, bodily tissue or a bodily fluid such as blood (or a fraction of blood such as plasma or serum), lymph, mucus, tears, saliva, sputum, urine, semen, stool, CSF, ascities fluid, or whole blood, and including biopsy samples of body tissue. A sample may also include an in vitro culture of microorganisms grown from a sample from a subject. A sample may be obtained from any subject, e.g., a subject/patient having or suspected to have tuberculosis.

As used herein, the term "screening" means determining whether a test compound has capabilities or characteristics of preventing or slowing down (lessening) the targeted pathologic condition stated herein, namely *M. tuberculosis* infection or any complications thereof.

As used herein, the term "subject" refers to a mammal, such as a human, but can also be another animal such as a domestic animal (e.g., a dog, cat, or the like), a farm animal (e.g., a cow, a sheep, a pig, a horse, or the like) or a laboratory animal (e.g., a monkey, a rat, a mouse, a rabbit, a guinea pig, or the like). The term "patient" refers to a "subject" who is, or is suspected to be, afflicted with tuberculosis.

As used herein, the term "treating" or "treatment" refers to both therapeutic treatment and prophylactic or preventative measures, wherein the object is to prevent, slow down, or lessen the targeted pathologic condition or disorder. A patient is successfully "treated" for a disorder if, after receiving a therapeutic amount of a test compound according to the methods of the present technology, the subject shows observable and/or measurable reduction in, or absence of, one or more signs or symptoms of tuberculosis.

Overview

Disclosed herein are methods for detecting the presence or absence of *Mycobacterium tuberculosis* infection in subjects based, at least in part, on results of testing methods of the present technology on a sample. Further disclosed herein are methods for monitoring the status of subjects diagnosed with *Mycobacterium tuberculosis* infection based at least partially on results of tests on a sample. The test samples disclosed herein are represented by, but not limited in anyway to, sputum, blood (or a fraction of blood such as plasma, serum, or particular cell fractions), lymph, mucus, tears, saliva, urine, semen, ascities fluid, whole blood, and biopsy samples of body tissue. A sample may also include an in vitro culture of microorganisms grown from a sample from a subject. This disclosure is drawn, inter alia, to methods of diagnosing, monitoring, and treating tuberculosis.

In one aspect, the methods generally provide for the detection, measuring, and comparison of a pattern of interaction between the one or more sigma factors and the one or more interacting proteins in the sample. Accordingly, the various aspects relate to the collection, preparation, separation, identification, characterization, and comparison of the abundance of sigma factor protein complexes in a test sample. The technology further relates to detecting and/or monitoring a sample containing one or more sigma factors and the one or more interacting proteins, which are useful, alone or in combination, to determine the presence or absence of tuberculosis or any progressive state thereof.

The pattern of interaction between one or more sigma factors and one or more interacting proteins is indicative of the environmental or developmental state of the bacillus, which, in turn, relates to the pathogenicity of the organism. By measuring these protein interactions, one can diagnose a patient, and/or select an appropriate treatment regime. Accordingly, another aspect includes selecting a treatment regime based on the absence, presence, or extent of tuberculosis in the subject.

The technology also pertains to selecting and monitoring the influence of agents (e.g., drugs, compounds) on the amount or type of sigma factor protein complexes as described in further detail in the following sections. In another aspect of the technology pertains to diagnostic kits for the detection and monitoring of tuberculosis.

Yet another aspect includes screening agents (e.g., drugs, compounds) that affect the pattern of sigma factor protein complexes in *M. tuberculosis* in order to identify those agents capable of modulating gene expression on the *bacillus*. These aspects of the disclosure will be described in further detail in the following sections.

Sigma Factor Protein Complexes

The pathogen *Mycobacterium tuberculosis* can survive in the host for several years until a failure in the host defense system leads to a re-activation of the disease. An essential requirement for this persistence is the ability of the bacillus to rapidly respond to changing environmental conditions in the host by modulating gene expression. A class of transcription factors, the so-called extra-cytoplasmic (ECF) sigma factors, are the key components of this system.

While not wishing to be limited by theory, the presence of multiple σ factors and the conditional association of these proteins with the RNA polymerase is a component of the prokaryotic transcriptional machinery that is sensitive to a diverse range of developmental and environmental stimuli. In specific conditions, the transcriptional response is also regulated by so-called appropriators that sequester the RNA polymerase (RNAP) to specific classes of promoters. σ factors participate in transcription initiation, providing the RNA polymerase with the ability to recognize promoter elements. Apart from the primary σ factor ($\sigma^A$) that is involved in essential housekeeping roles, the so-called Extra Cytoplasmic Function (ECF) σ factors are recruited to effect environment-dependent changes in transcription. Most ECF σ factors are post-translationally regulated. They are bound in an inactive conformation with an anti-σ factor and are released upon different environmental stimuli. The anti-σ factor, in most cases, is co-transcribed with the σ factor and occurs as part of the same operon. Although several of these anti-σ factors are membrane bound proteins that directly respond to external stimuli, several cytosolic variants have also been reported to function as anti-σ.

*M. tuberculosis* has at least 13 σ-factors and at least one alternate σ-factor, pvdS. Four sigma factors, $\sigma^A$, $\sigma^B$, $\sigma^C$ and $\sigma^E$ of the 13 in *M. tuberculosis* are conserved in all the pathogenic mycobacteria. Five σ-factors-$\sigma^A$, $\sigma^B$, $\sigma^D$, $\sigma^E$ and $\sigma^F$ are essential genes in *M. tuberculosis*. The σ-factors $\sigma^A$, $\sigma^B$ and $\sigma^F$ are classified as the principal/principal like σ-factors, a class which includes the *E. coli* $\sigma^{70}$ and its orthologues. These factors are essential proteins responsible for transcription in most rapidly growing bacterial cells. $\sigma^B$ and $\sigma^F$ have been implicated in stress and stringent responses in *M. tuberculosis*. Group 2 σ factors are non-essential proteins that are similar to the $\sigma^{70}$ family. Based on the similarity observed in stretches of the amino acid sequence that are thought to govern promoter specificity in both group 1 as well as group 2, it is likely that they have an extensive overlap in promoter recognition. Group 3 sigma factors are secondary sigma factors of the $\sigma^{70}$ family and are significantly smaller in size than their group 1 or group 2 paralogues (typically 25 to 35 kDa in molecular mass). These σ-factors function as global regulators allowing the coordinate activation of numerous unlinked operons. As a class, the group 3 σ-factors are regulated in diverse ways: some at the level of synthesis, others by proteolysis, and others by their reversible interaction with an anti-σ factor. The ECF σ-factors belong to Group 4. These σ-factors link the signal transduction and transcription regulation mechanisms. Group 5 in the classification of σ-factors includes members of the TxeR subfamily, proteins that recognize tox promoters and control toxin gene expression.

Most ECF sigma factors are cotranscribed with one or more negative regulators. Often, these include a transmembrane protein functioning as an "anti-sigma factor" that binds, and inhibits, the cognate sigma factor. Upon receiving a stimulus from the environment, the sigma factor is released and can bind to RNA polymerase to stimulate transcription. The *M. tuberculosis* sigma factors are listed in Table 1. The GenBank reference numbers for the cDNA sequences encoding the proteins are also noted in the table.

TABLE 1

*M. Tuberculosis* Sigma Factors

| Sigma Factor | Length (aa) | Type | GenBank Accession No. |
| --- | --- | --- | --- |
| $\sigma^A$, Rv2703 | 528 | Principal | U10059 |
| $\sigma^B$, Rv2710 | 323 | Principal-like | U10059 |
| $\sigma^F$, Rv3286c | 261 | Stress-sporulation | U41061 |
| $\sigma^E$, Rv1221 | 257 | ECF | U87242 |
| $\sigma^C$, Rv2069 | 222 | ECF | Z73966 |
| $\sigma^D$, Rv3414x | 212 | ECF | Z77165 |
| $\sigma^G$, Rv0182 | 222 | ECF | AL021426 |
| $\sigma^H$, Rv3223 | 216 | ECF | Z95012 |
| $\sigma^I$, Rv1189 | 249 | ECF | AL01086 |
| $\sigma^J$, Rv3328 | 213 | ECF | AL021841 |
| $\sigma^K$, Rv0445c | 188 | ECF | AL012932 |
| $\sigma^L$, Rv0735 | 177 | ECF | AL012958 |
| $\sigma^M$, Rv3911 | 223 | ECF | AL021426 |

A number of developmental and environmental stimuli are relevant to the pathogenicity of *M. tuberculosis*. These include, but are not limited to, early exponential phase growth, late exponential phase growth, stationary phase growth, sporulation, oxidative stress, disulfide response, alcohol shock, and nitrogen depletion. An illustrative, but not exhaustive, list of the sigma factors and the corresponding interacting proteins (anti-sigma factors) involved in responding to these developmental or environmental stimuli are shown in Table 2.

TABLE 2

Exemplary Protein Complexes Involved in Environmental/Developmental Responses

| Name (Rv number) | Interacting partners | Environmental Conditions |
| --- | --- | --- |
| SigA (Rv2703) | whiB3 | Constitutively expressed |
| SigB (Rv2710) | SigE, SigH, IdeR | Heat shock, SDS-mediated surface stress, oxidative stress mediated by diamide and carbon starvation. |
| SigC (Rv2069) | SigH, SigM, blaA, Rv2067 | Exponential phase, $H_2O_2$ & diamide. |
| SigD (Rv3414c) | Rv3413c, SigM | Nutrient starvation |
| SigE (Rv1221) | Rv1222, htrA, TatB | SDS-mediated surface stress, heat shock, vancomycin mediated cell surface stress, diamide oxidative stress and in human macrophages. |
| SigF (Rv3286c) | usfX, Rv1364c, Rv1365c | Oxidative stress, nutrient depletion, cold shock, anaerobiosis (metronidazole) & stationary phase. |
| SigG (Rv0182c) | SigK, Rv0180c, Rv0181c, Rv0183, Rv2250c | Human macrophages. |

TABLE 2-continued

Exemplary Protein Complexes Involved in Environmental/Developmental Responses

| Name (Rv number) | Interacting partners | Environmental Conditions |
| --- | --- | --- |
| SigH (Rv3223c) | SigB, SigC, SigK, SigI | Heat shock, macrophage infection, and oxidative stress (thiol specific oxidizing agent diamide). |
| SigI (Rv1189) | SigH, Rv1190, Rv1188 | Cold shock |
| SigJ (Rv3328c) | Rv3329, PBP (DACB1), tetR family. | Stationary phase cultures, human macrophages and may have a role in oxidative stress response. |
| SigK (Rv0445c) | dipZ, mpt70, mpt83, SigM, Rv0444c. | |
| SigL (Rv0735) | Rv0760, SigM, map1, adk | SDS and superoxide generator plumbagine. |
| SigM (Rv3911) | Rv3910, Rv3909, Rv3908, SigK, SigD, SigC | Heat shock. |
| PvdS (Rv3232c) | Rv3231c, Rv3233c, Rv0917 | |

Detection Methods for Protein Complexes

In one aspect, the disclosure relates to methods for detecting the protein complexes, particularly for determining the concentration of a specific protein complex in a patient sample or a bacterial sample obtained from a patient. Protein complexes may also be detected in the context of the screening assays described in further detail below.

In practicing the present technology, many conventional techniques in molecular biology, protein biochemistry, cell biology, immunology, and microbiology are used. These techniques are well-known and are explained in, e.g., *Current Protocols in Molecular Biology*, Vols. I-III, Ausubel, Ed. (1997); Sambrook et al., *Molecular Cloning: A Laboratory Manual*, Second Ed. (Cold Spring Harbor Laboratory Press, Cold Spring Harbor, N.Y., 1989); *DNA Cloning: A Practical Approach*, Vols. I and II, Glover, Ed. (1985); *Transcription and Translation*, Hames & Higgins, Eds. (1984); *Animal Cell Culture*, Freshney, Ed. (1986); *Immobilized Cells and Enzymes* (IRL Press, 1986); Perbal, *A Practical Guide to Molecular Cloning;* the series, *Meth. Enzymol.*, (Academic Press, Inc., 1984); *Gene Transfer Vectors for Mammalian Cells*, Miller & Calos, Eds. (Cold Spring Harbor Laboratory, NY, 1987); and *Meth. Enzymol.*, Vols. 154 and 155, Wu & Grossman, and Wu, Eds., respectively. Methods to detect and measure the levels of protein complexes are well-known in the art and include ELISA assays, and co-immunoprecipitation assays.

In one embodiment, the level of expression of one or more protein complexes involving one or more sigma factors and one or more interacting proteins may be measured by determining the amount of the protein complexes in a sample. The polypeptides can be detected by an antibody which is detectably labeled, or which can be subsequently labeled. A variety of formats can be employed to determine whether a sample contains a target protein or proteins that binds to a given antibody. Immunoassay methods useful in the detection of protein complexes include, but are not limited to, e.g., dot blotting, western blotting, protein chips, immunoprecipitation (IP), competitive and non-competitive protein binding assays, enzyme-linked immunosorbant assays (ELISA), and others commonly used and widely-described in scientific and patent literature, and many employed commercially. A skilled artisan can readily adapt known protein/antibody detection methods for use in determining whether samples contain a biomarker and the relative concentration or variant form of that specific polypeptide expression product in the sample. Proteins from bacterial samples can be isolated using techniques that are well-known to those of skill in the art. The protein isolation methods employed can, e.g., be including, but not limited to, e.g., those described in Harlow & Lane, *Antibodies: A Laboratory Manual* (Cold Spring Harbor Laboratory Press, Cold Spring Harbor, N.Y., 1988).

Antibodies can be used in methods, including, but not limited to, e.g., western blots or ELISA, to detect the expressed protein complexes. In such uses, it is possible to immobilize either the antibody or proteins on a solid support. Supports or carriers include any support capable of binding an antigen or an antibody. Well-known supports or carriers include, but are not limited to, e.g., glass, polystyrene, polypropylene, polyethylene, dextran, nylon, amylases, natural and modified celluloses, polyacrylamides, gabbros, and magnetite.

In one embodiment, the concentration of a protein complex of one or more sigma factors and one or more interacting proteins is determined in a patient sample or a bacterial sample obtained from a patient. For example, the protein complex can be isolated or purified from a sample obtained from cells, tissue, or an organ of the patient and the amount thereof is determined. The protein complex can be prepared from cells, tissue or organ samples by coimmunoprecipitation using an antibody immunoreactive with an interacting protein member, a bifunctional antibody that is immunoreactive with two or more interacting protein members of the protein complex, or an antibody selectively immunoreactive with the protein complex. When bifunctional antibodies or antibodies immunoreactive with only free interacting protein members are used, individual interacting protein members not complexed with other proteins may also be isolated along with the protein complex containing such individual proteins. However, they can be readily separated from the protein complex using methods known in the art, e.g., size-based separation methods such as gel filtration, or by subtracting the protein complex from the mixture using an antibody specific against another individual interacting protein member. Additionally, proteins in a sample can be separated in a gel such as polyacrylamide gel and subsequently immunoblotted using an antibody immunoreactive with the protein complex.

Alternatively, the concentration of the protein complex can be determined in a sample without separation, isolation or purification. For this purpose, an antibody selectively immunoreactive with the specific protein complex may be used in an immunoassay. For example, immunocytochemical methods can be used. Other well known antibody-based techniques can also be used including, e.g., enzyme-linked immunosorbent assay (ELISA), radioimmunoassay (RIA), immunoradiometric assays (IRMA), fluorescent immunoassays, protein A immunoassays, and immunoenzymatic assays (IEMA).

In addition, since a specific protein complex is formed from its interacting protein members, if one of the interacting protein members is at a relatively low concentration in a sample, it may be reasonably expected that the concentration of the protein complex in the sample may also be low. Therefore, the concentration of an individual interacting protein member of a specific protein complex can be determined in a patient sample which can then be used as a reasonably accurate indicator of the concentration of the protein complex in the sample. For this purpose, antibodies against an individual interacting protein member of a specific complex can be used in any one of the methods described above. In one embodiment, the concentration of each of the interacting protein members of a protein complex is determined in a sample and the relative concentration of the protein complex is then deduced.

As discussed above, the interaction between members of an interacting protein pair suggests that the protein complexes formed by such proteins may be involved in common biological processes, such as responses to environmental or developmental conditions. These complexes may be used as parameters for classifying and/or staging tuberculosis in a subject. In addition, they may also be indicators for patients' response to a drug therapy.

Association between a pathological state (e.g., latent or active tuberculosis) and the presence or aberration of a protein complex can be readily determined by comparative analysis of the protein complex and/or the interacting members thereof in a normal population and an abnormal or affected population. Thus, for example, one can study the concentration of a particular protein complex, mutations in the interacting protein members of the protein complex, and/or the binding affinity between the interacting protein members in both a normal population and a population affected with a particular pathological state. The study results can be compared and analyzed by statistical means. Any detected statistically significant difference in the two populations would indicate an association. For example, if the concentration of the protein complex is statistically significantly higher in the affected population than in the normal population, then it can be reasonably concluded that higher concentration of the protein complex is associated with the pathological state.

Statistical methods can be used to set thresholds for determining when the expression level in a subject can be considered to be different than or similar to a reference level. In addition, statistics can be used to determine the validity of the difference or similarity observed between a patient's gene expression level and the reference level. Useful statistical analysis methods are described in L. D. Fisher & G. vanBelle, *Biostatistics: A Methodology for the Health Sciences* (Wiley-Interscience, NY, 1993). For instance, confidence ("p") values can be calculated using an unpaired 2-tailed t test, with a difference between groups deemed significant if the p value is less than or equal to 0.05.

Once an association is established between an aberration in a particular protein complex and a pathological state, then the particular physiological state can be diagnosed or detected by determining whether a patient has the particular aberration. As used herein, the term "aberration" when used in the context of protein complexes means any detectable alterations of a protein complex including increased or decreased concentration of the protein complex in a particular cell, changes in binding affinity of an interacting protein member of the protein complex, mutations in an interacting protein member or the gene encoding the protein, and the like. As will be apparent to a skilled artisan, the term "aberration" is used in a relative sense. That is, an aberration is relative to a normal condition. For example, a detectable aberration may be a difference in the level the particular protein interaction present in a sample as compared to a control of at least about 1%, at least about 2%, at least about 3%, at least about 5%, at least about 10%, at least about 15%, at least about 20%, at least about 25%, at least about 30%, at least about 35%, at least about 40%, at least about 50%, at least about 60%, at least about 75%, at least about 80% or more.

Thus, in one embodiment, the method of diagnosis is conducted by detecting, in a patient, the concentrations of one or more protein complexes using any one of the methods described above, and determining whether the patient has an aberrant concentration of the protein complexes. The diagnosis may also be based on the determination of the concentrations of one or more interacting protein members of a protein complex. An aberrant concentration of an interacting protein member may indicate particular pathological state or the status of the bacillus in the subject.

In some embodiments, the detectable quantity of a protein complex or the difference in the level of a protein complex compared between a test sample and a control is an amount over the background level for a particular assay. The term "background level" encompasses non-specific measurements of protein complexes that may be present in a sample lacking the protein complex of interest. In one embodiment, a detectable amount of the protein complex will be anything over zero. In another embodiment, where protein complex is normally found in the particular sample at a background level, then a detectable amount of the protein complex will be an amount over the background level sufficient to differentiate the added material over the background level of protein complex.

In another embodiment, the method of diagnosis includes detecting any mutations in one or more interacting protein members of a protein complex. In particular, it may be desirable to determine whether the interacting protein members have any mutations that will lead to, or are associated with, changes in the functional activity of the proteins or changes in their binding affinity to other interacting protein members in forming a protein complex. Examples of such mutations include but are not limited to, e.g., deletions, insertions and rearrangements in the genes encoding the protein members, and nucleotide or amino acid substitutions and the like. In another embodiment, the domains of the interacting protein members that are responsible for the protein-protein interactions, and lead to protein complex formation, are screened to detect any mutations therein. For example, DNA encoding an interacting protein member can be prepared from a bacterial sample, and sequenced. The sequence may be compared with known wild-type sequences to identify any mutations. Alternatively, an interacting protein member may be purified from a sample and analyzed by protein sequencing or mass spectrometry to detect any amino acid sequence changes. Any methods known in the art for detecting mutations may be used.

In another embodiment, the method of diagnosis includes determining the binding constant of the interacting protein members of one or more protein complexes. For example, the interacting protein members can be obtained from a sample by direct purification or by recombinant expression from genomic DNAs. Binding constants represent the strength of the protein-protein interaction between the interacting protein members in a protein complex. Thus, by measuring binding constants, subtle aberrations in binding affinity may be detected.

A number of methods known in the art for estimating and determining binding constants in protein-protein interactions. For example, protein affinity chromatography may be used. First, columns are prepared with different concentrations of an interacting protein member, which is covalently bound to the columns. Then a preparation of an interacting protein partner is run through the column and washed with buffer. The interacting protein partner bound to the interacting protein member linked to the column is then eluted. A binding constant is then estimated based on the concentrations of the bound protein and the eluted protein. Alternatively, the method of sedimentation through gradients monitors the rate of sedimentation of a mixture of proteins through gradients of glycerol or sucrose. At concentrations above the binding constant, proteins can sediment as a protein complex. Thus, binding constant can be calculated based on the concentrations. Other suitable methods known in the art for estimating binding constant include but are not limited to gel filtration column such as nonequilibrium "small-zone" gel filtration columns (See e.g., Gill et al., *J. Mol. Biol.*, 220:307-324 (1991)), the Hummel-Dreyer method of equilibrium gel filtration (See e.g., Hummel and Dreyer, *Biochim. Biophys. Acta,* 63:530-532 (1962)) and large-zone equilibrium gel filtration (See e.g., Gilbert and Kellett, *J. Biol. Chem.,* 246: 6079-6086 (1971)), sedimentation equilibrium (See e.g., Rivas and Minton, *Trends Biochem.*, 18:284-287 (1993)), fluorescence methods such as fluorescence spectrum (See e.g., Otto-Bruc et al., Biochemistry, 32:8632-8645 (1993)) and fluorescence polarization or anisotropy with tagged molecules (See e.g., Weiel and Hershey, *Biochemistry,* 20:5859-5865 (1981)), solution equilibrium measured with immobilized binding protein (See e.g., Nelson and Long, *Biochemistry,* 30:2384-2390 (1991)), and surface plasmon resonance (See e.g., Panayotou et al., *Mol. Cell. Biol.,* 13:3567-3576 (1993)).

In another embodiment, a protein microchip or microarray is provided having one or more of the protein complexes and/or antibodies selectively immunoreactive with the protein complexes attached. The protein microarrays in accordance with this embodiment will be useful in a variety of applications including, e.g., large-scale or high-throughput screening for compounds capable of binding to the protein complexes or modulating the interactions between the interacting protein members in the protein complexes.

The protein microarray can be prepared in a number of methods known in the art. For example, glass microscope slides are treated with an aldehyde-containing silane reagent (SuperAldehyde Substrates purchased from TeleChem International, Cupertino, Calif.). Nanoliter volumes of protein samples in a phosphate-buffered saline with 40% glycerol are then spotted onto the treated slides using a high-precision contact-printing robot. After incubation, the slides are immersed in a bovine serum albumin (BSA)-containing buffer to quench the unreacted aldehydes and to form a BSA layer that functions to prevent non-specific protein binding in subsequent applications of the microchip. Alternatively, proteins or protein complexes can be attached to a BSA-NHS slide by covalent linkages. BSA-NHS slides are fabricated by first attaching a molecular layer of BSA to the surface of glass slides and then activating the BSA with N,N'-disuccinimidyl carbonate. As a result, the amino groups of the lysine, aspartate, and glutamate residues on the BSA are activated and can form covalent urea or amide linkages with protein samples spotted on the slides.

Another example of a protein microchip includes a substrate or chip base covered with one or more layers of thin organic film to eliminate any surface defects, insulate proteins from the base materials, and to ensure uniform protein array. Next, a plurality of protein-capturing agents (e.g., antibodies, peptides, etc.) are arrayed and attached to the base that is covered with the thin film. Proteins or protein complexes can then be bound to the capturing agents forming a protein microarray. The protein microchips are kept in flow chambers with an aqueous solution.

In another example, a three-dimensional hydrophilic polymer matrix, i.e., a gel, is first dispensed on a solid substrate such as a glass slide. The polymer matrix gel is capable of expanding or contracting and contains a coupling reagent that reacts with amine groups. Thus, proteins and protein complexes can be contacted with the matrix gel in an expanded aqueous and porous state to allow reactions between the amine groups on the protein or protein complexes with the coupling reagents thus immobilizing the proteins and protein complexes on the substrate. Thereafter, the gel is contracted to embed the attached proteins and protein complexes in the matrix gel.

In some embodiments, antibodies immunoreactive against a sigma factor and/or an interacting protein are provided. Alternatively, an antibody immunoreactive against a protein complex is provided. In one embodiment, the antibody is selectively immunoreactive with a protein complex. Specifically, the phrase "selectively immunoreactive with a protein complex" as used herein means that the immunoreactivity of the antibody with the protein complex is substantially higher than that with the individual interacting members of the protein complex so that the binding of the antibody to the protein complex is readily distinguishable from the binding of the antibody to the individual interacting member proteins based on the strength of the binding affinities. In some embodiments, the binding constants differ by a magnitude of at least 2 fold, at least 5 fold, at least 10 fold, or at least 100 fold. In a specific embodiment, the antibody is not substantially immunoreactive with the interacting protein members of the protein complex.

The antibodies can be readily prepared using procedures generally known in the art. See, e.g., Harlow and Lane, *Antibodies: A Laboratory Manual*, Cold Spring Harbor Press, 1988. Typically, the protein against which an immunoreactive antibody is desired is used as the antigen for producing an immune response in a host animal. In one embodiment, the protein complex used consists of the native proteins. If antibodies against the protein complex are desired, the antigen may include only protein fragments containing interacting regions. As a result, a greater portion of the total antibodies may be selectively immunoreactive with the protein complexes. In addition, various techniques known in the art for predicting epitopes may also be employed to design antigenic peptides based on the interacting protein members in a protein complex to increase the possibility of producing an antibody selectively immunoreactive with the protein complex. Suitable epitope-prediction computer programs include, e.g., MacVector from International Biotechnologies, Inc. and Protean from DNAStar.

The antibodies can be a polyclonal antibody to a protein or protein complex. To produce the polyclonal antibody, various animal hosts can be employed, including, e.g., mice, rats, rabbits, goats, guinea pigs, hamsters, etc. A suitable antigen can be administered directly to a host animal to elicit immune reactions. Alternatively, it can be administered together with a carrier such as keyhole limpet hemocyanin (KLH), bovine serum albumin (BSA), ovalbumin, and Tetanus toxoid. Optionally, the antigen may be conjugated to a carrier by a coupling agent such as carbodiimide, glutaraldehyde, and MBS. Any conventional adjuvants may be used to boost the immune response of the host animal to the protein complex antigen. Suitable adjuvants known in the art include, but are not limited to, Complete Freund's Adjuvant, incomplete Freund's Adjuvant, aluminum salts, MF59 from Chiron (Emeryville, Calif.), monophospholipid, synthetic trehalose dicorynomycolate (TDM) and cell wall skeleton (CWS) both from Corixa Corp. (Seattle, Wash.), non-ionic surfactant vesicles (NISV) from Proteus International PLC (Cheshire, U.K.), and saponins. The antigen preparation can be administered to a host animal by subcutaneous, intramuscular, intravenous, intradermal, or intraperitoneal injection, or by injection into a lymphoid organ.

The antibodies may also be monoclonal. Such monoclonal antibodies may be developed using any conventional techniques known in the art. For example, the hybridoma method is now a well-developed technique that can be used. Essentially, B-lymphocytes producing a polyclonal antibody against a protein complex can be fused with myeloma cells to generate a library of hybridoma clones. The hybridoma population is then screened for antigen binding specificity and also for immunoglobulin class (isotype). In this manner, pure hybridoma clones producing specific homogenous antibodies can be selected. See generally, Harlow and Lane, *Antibodies: A Laboratory Manual*, Cold Spring Harbor Press, 1988. Alternatively, other techniques known in the art may also be used to prepare monoclonal antibodies, which include but are not limited to the EBV hybridoma technique, the human N-cell hybridoma technique, and the trioma technique.

In addition, antibodies selectively immunoreactive with a protein or protein complex may also be recombinantly produced. For example, cDNAs prepared by PCR amplification from activated B-lymphocytes or hybridomas may be cloned into an expression vector to form a cDNA library, which is then introduced into a host cell for recombinant expression. The cDNA encoding a specific desired protein may then be isolated from the library. The isolated cDNA can be introduced into a suitable host cell for the expression of the protein. Thus, recombinant techniques can be used to produce specific native antibodies, hybrid antibodies capable of simultaneous reaction with more than one antigen, chimeric antibodies (e.g., the constant and variable regions are derived from different sources), univalent antibodies that comprise one heavy and light chain pair coupled with the Fc region of a third (heavy) chain, Fab proteins, and the like. Antibody fragments such as Fv fragments, single-chain Fv fragments (scFv), Fab' fragments, and $F(ab')_2$ fragments can also be recombinantly produced.

In another embodiment, a bifunctional antibody is provided that has two different antigen binding sites, each being specific to a different interacting protein member in a protein complex. The bifunctional antibody may be produced using a variety of methods known in the art. For example, two different monoclonal antibody-producing hybridomas can be fused together. One of the two hybridomas may produce a monoclonal antibody specific against an interacting protein member of a protein complex, while the other hybridoma generates a monoclonal antibody immunoreactive with another interacting protein member of the protein complex. The new hybridoma produces different antibodies including a desired bifunctional antibody, i.e., an antibody immunoreactive with both of the interacting protein members. The bifunctional antibody can be readily purified.

Alternatively, a bifunctional antibody may also be produced using heterobifunctional crosslinkers to chemically link two different monoclonal antibodies, each being immunoreactive with a different interacting protein member of a protein complex. Therefore, the aggregate will bind to two interacting protein members of the protein complex. In addition, bifunctional antibodies can also be produced by recombinantly expressing light and heavy chain genes in a hybridoma that itself produces a monoclonal antibody. As a result, a mixture of antibodies including a bifunctional antibody is produced.

A bifunctional antibody may be produced by mixing two different Fabs. The first Fab can bind to an interacting protein member of a protein complex, and has a heavy chain constant region having a first complementary domain not naturally present in the Fab but capable of binding a second complementary domain. The second Fab is capable of binding another interacting protein member of the protein complex, and has a heavy chain constant region comprising a second complementary domain not naturally present in the Fab but capable of binding to the first complementary domain. Each of the two complementary domains is capable of stably binding to the other but not to itself.

Methods of Preparing Protein Complexes. In some embodiments, protein complexes are prepared for the purpose of screening therapeutic compounds or as positive controls in diagnostic or prognostic assays. Protein complexes can be prepared by a variety of methods. Specifically, a protein complex can be isolated directly from a bacterial sample containing the protein complex. Alternatively, a protein complex can be purified from host cells that recombinantly express the members of the protein complex. As will be apparent to a skilled artisan, a protein complex can be prepared from a bacterial sample or recombinant host cells by co-immunoprecipitation using an antibody immunoreactive with an interacting protein partner, or an antibody selectively immunoreactive with the protein complex as will be discussed above.

Co-immunoprecipitation is a commonly used method in the art for isolating or detecting bound proteins. In this procedure, generally a sample or cell lysate is admixed with a suitable antibody. The antibodies can be monoclonal or polyclonal. The protein complex bound to the antibody is precipitated and washed. The bound protein complexes are then eluted.

Alternatively, immunoaffinity chromatography and immunoblotting techniques may also be used in isolating the protein complexes from tissue or bacterial samples or recombinant host cells using an antibody immunoreactive with an interacting protein partner, or an antibody selectively immunoreactive with the protein complex. For example, in protein immunoaffinity chromatography, the antibody is covalently or non-covalently coupled to a matrix (e.g., Sepharose), which is then packed into a column. Extract from a bacterial sample, or lysate from recombinant cells is passed through the column where it contacts the antibodies attached to the matrix. The column is then washed with a low-salt solution to wash away the unbound or loosely (non-specifically) bound components. The protein complexes that are retained in the column can be then eluted from the column using a high-salt solution, a competitive antigen of the antibody, a chaotropic solvent, or sodium dodecyl sulfate (SDS), or the like. In immunoblotting, crude proteins samples from a tissue sample extract or recombinant host cell lysate are fractionated by polyacrylamide gel electrophoresis (PAGE) and then transferred to a membrane, e.g., nitrocellulose. Components of the protein complex can then be located on the membrane and identified by a variety of techniques, e.g., probing with specific antibodies.

In another embodiment, individual interacting protein partners may be isolated or purified independently from tissue samples or recombinant host cells using similar methods as described above. The individual interacting protein partners are then combined under conditions conducive to their interaction, thereby forming a protein complex. It is noted that different protein-protein interactions may require different conditions. As a starting point, for example, a buffer having 20 mM Tris-HCl, pH 7.0 and 500 mM NaCl may be used. Several different parameters may be varied, including temperature, pH, salt concentration, reducing agent, and the like. Some minor degree of experimentation may be required to determine the optimum incubation condition, this being well within the capability of one skilled in the art.

In yet another embodiment, the protein complex may be prepared from bacterial samples or recombinant host cells or other suitable sources by protein affinity chromatography or affinity blotting. That is, one of the interacting protein partners is used to isolate the other interacting protein partner(s) by binding affinity thus forming protein complexes. Thus, an interacting protein partner prepared by purification from tissue samples or by recombinant expression or chemical synthesis may be bound covalently or non-covalently to a matrix, e.g., Sepharose, which is then packed into a chromatography column. The tissue sample extract or cell lysate from the recombinant cells can then be contacted with the bound protein on the matrix. A low-salt solution is used to wash off the unbound or loosely bound components, and a high-salt solution is then employed to elute the bound protein complexes in the column. In affinity blotting, crude protein samples from a tissue sample or recombinant host cell lysate can be fractionated by polyacrylamide gel electrophoresis (PAGE) and then transferred to a membrane, e.g., nitrocellulose. The purified interacting protein member is then bound to its interacting protein partner(s) on the membrane forming protein complexes, which are then isolated from the membrane.

It will be apparent to skilled artisans that any recombinant expression methods may be used for purposes of expressing the protein complexes or individual interacting proteins. Generally, a nucleic acid encoding an interacting protein member can be introduced into a suitable host cell. For purposes of forming a recombinant protein complex within a host cell, nucleic acids encoding two or more interacting protein members should be introduced into the host cell.

Typically, the nucleic acids, in the form of DNA, are incorporated into a vector to form expression vectors capable of directing the production of the interacting protein member(s) once introduced into a host cell. Methods for the construction of an expression vector should be apparent to skilled artisans apprised of the present disclosure. Generally, the expression vectors include an expression cassette having a promoter operably linked to a DNA encoding a sigma factor or an interacting protein member. The promoter can be a native promoter, i.e., the promoter found in naturally occurring cells to be responsible for the expression of the interacting protein member in the cells. Alternatively, the expression cassette can be a chimeric one, i.e., having a heterologous promoter that is not the native promoter responsible for the expression of the interacting protein member in naturally occurring cells. The expression vector may further include an origin of DNA replication for the replication of the vectors in host cells and selection marker(s) for selecting and maintaining only those host cells harboring the expression vectors. Additionally, the expression cassettes may also contain inducible elements, which function to control the transcription from the DNA encoding an interacting protein member. Other regulatory sequences such as transcriptional enhancer sequences and translation regulation sequences (e.g., Shine-Dalgarno sequence) can also be operably included in the expression cassettes. Termination sequences such as the polyadenylation signals from bovine growth hormone, SV40, lacZ and AcMNPV polyhedral protein genes may also be operably linked to the DNA encoding an interacting protein member in the expression cassettes. An epitope tag coding sequence for detection and/or purification of the expressed protein can also be operably linked to the DNA encoding an interacting protein member such that a fusion protein is expressed. Examples of useful epitope tags include, but are not limited to, influenza virus hemagglutinin (HA), Simian Virus 5 (V5), polyhistidine (6×His), c-myc, lacZ, GST, and the like. Proteins with polyhistidine tags can be easily detected and/or purified with Ni affinity columns, while specific antibodies immunoreactive with many epitope tags are generally commercially available. When it is desirable to express two or more interacting protein members in a single host cell, the DNA fragments encoding the interacting protein members may be incorporated into a single vector or different vectors.

The constructed expression vectors can be introduced into the host cells by any techniques known in the art, e.g., by direct DNA transformation, microinjection, electroporation, viral infection, lipofection, gene gun, and the like. The expression of the interacting protein members may be transient or stable. The expression vectors can be maintained in host cells in an extrachromosomal state, i.e., as self-replicating plasmids or viruses. Alternatively, the expression vectors can be integrated into chromosomes of the host cells by conventional techniques such as selection of stable cell lines or site-specific recombination. In stable cell lines, at least the expression cassette portion of the expression vector is integrated into a chromosome of the host cells.

The vector construct can be designed to be suitable for expression in various host cells, including but not limited to bacteria, yeast cells, plant cells, insect cells, and mammalian and human cells. Methods for preparing expression vectors for expression in different host cells should be apparent to a skilled artisan.

Screening Assays

The protein complexes and interacting members thereof can also be used in screening assays to identify modulators of the protein complexes, and/or the interacting proteins. In addition, homologues, derivatives or fragments of the interacting proteins may also be used in such screening assays. As used herein, the term "modulator" encompasses any compound that can cause any form of alteration of the biological activities or functions of the proteins or protein complexes compared to the biological activities or functions of the proteins or protein complexes in a normal or control environment. For example, modulators may act on protein complexes by enhancing or reducing their biological activities, increasing or decreasing their stability, altering their affinity or specificity to certain other biological molecules, etc., In addition, the term "modulator" as used herein also includes any compounds that simply bind any of the proteins described in the tables, and/or the proteins complexes. For example, a modulator can be an "interaction antagonist" capable of interfering with or disrupting or dissociating protein-protein interaction between an interacting pair of proteins identified in the tables, or homologues, fragments or derivatives thereof. A modulator can also be an "interaction agonist" that initiates or strengthens the interaction between the protein members of a protein complex, or homologues, fragments or derivatives thereof. The selected compounds can be tested for their ability to modulate (interfere with or strengthen) the interaction between the interacting partners within the protein complexes.

The modulators selected in accordance with the screening methods can be effective in modulating the functions or activities of individual interacting proteins, or the protein complexes. For example, compounds capable of binding to the protein complexes may be capable of modulating the functions of the protein complexes. Additionally, compounds that interfere with, weaken, dissociate or disrupt, or alternatively, initiate, facilitate or stabilize the protein-protein interaction between the interacting protein members of the protein complexes can also be effective in modulating the functions or activities of the protein complexes. Thus, the compounds identified in the screening methods can be made into therapeutically or prophylactically effective drugs for preventing or ameliorating tuberculosis or complications thereof. The protein complexes and/or interacting protein members thereof can be used in any of a variety of drug screening techniques.

Any test compounds may be screened in the screening assays to select modulators of the protein complexes or interacting members thereof. By the term "selecting" or "select" compounds it is intended to encompass both (a) choosing compounds from a group previously unknown to be modulators of a protein complex or interacting protein members thereof, and (b) testing compounds that are known to be capable of binding, or modulating the functions and activities of, a protein complex or interacting protein members thereof. Both types of compounds are generally referred to herein as "test compounds." The test compounds may include, by way of example, proteins (e.g., antibodies, small peptides, artificial or natural proteins), nucleic acids, and derivatives, mimetics and analogs thereof, and small organic molecules having a molecular weight of no greater than 10,000 daltons. The test compounds may be provided in library formats known in the art, e.g., in chemically synthesized libraries, recombinantly expressed libraries (e.g., phage display libraries), and in vitro translation-based libraries (e.g., ribosome display libraries).

Peptidic test compounds may be peptides having L-amino acids and/or D-amino acids, phosphopeptides, and other types of peptides. The screened peptides can be of any size, and may have less than about 50 amino acids. Smaller peptides are easier to deliver into a patient's body. Various forms of modified peptides may also be screened. Like antibodies, peptides can also be provided in, e.g., combinatorial libraries. For example, random-sequence peptide phage display libraries may be generated by cloning synthetic oligonucleotides into the gene III or gene VIII of an *E. coli* filamentous phage. The phage can propagate in *E. coli.* and express peptides encoded by the oligonucleotides as fusion proteins on the surface of the phage. Alternatively, the "peptides on plasmids" method may also be used to form peptide libraries. In this method, random peptides may be fused to the C-terminus of the *E. coli*. Lac repressor by recombinant technologies and expressed from a plasmid that also contains Lac repressor-binding sites. As a result, the peptide fusions bind to the same plasmid that encodes them.

Small organic or inorganic non-peptide non-nucleotide compounds may be used as test compounds for the screening assays. They too can be provided in a library format. Other compounds such as oligonucleotides and peptide nucleic acids (PNA), and analogs and derivatives thereof may also be screened to identify clinically useful compounds. Combinatorial libraries of oligonucleotides are also known in the art. See Gold et al., J. Biol. Chem., 270:13581-13584 (1995).

Potential agents can be screened for use in regulating the growth of *M. tuberculosis* by their ability to regulate the interaction of one or more sigma factors with one or more interacting proteins. The ability of a test compound or a potential therapeutic agent to regulate the interaction of one or more sigma factors with one or more interacting proteins is assessed by measuring the transcription of a gene in a transcription construct in vitro. A transcription construct comprises a promoter responsive to one or more *M. tuberculosis* sigma factors and a gene. The gene in the transcription construct could be any gene known in the art. In one embodiment, the length of the transcript of the gene is less than 200 bp and no more than 600 bp. The promoter in the transcription construct can be any to which one or more *M. tuberculosis* sigma factors binds and which it activates. The promoter is responsive to one or more *M. tuberculosis* sigma factors which induces the transcription of the gene downstream from and adjacent to the promoter. Suitable methods for measuring in vitro transcription are any known in the art. In vitro transcription may be carried out by incubating a transcription construct with one or more *M. tuberculosis* sigma factors, labeled nucleotides, e.g., $^{32}$P-ATP, core RNA polymerase, nucleotides, and buffer reagents in the presence and absence of a test compound. The procedures for purifying core RNA polymerase from mycobacteria are well described in the art. The conditions for in vitro transcription are also well known in the art. The labeled transcript can be detected by gel electrophoresis.

A potential therapeutic agent which increases the level of in vitro transcription indicates its ability to enhance the activity of the one or more *M. tuberculosis* sigma factors. Test compounds which increase the activity of the one or more *M. tuberculosis* sigma factors may trigger the growth arrest of *M. tuberculosis*. These compounds can be administered to a human with active tuberculosis, especially those who respond poorly to conventional antibiotic treatments. These compounds can induce growth arrest of *M. tuberculosis*, and initiate dormancy during severely advanced progressive tuberculosis or multi-drug resistant tuberculosis.

A test substance which decreases the production of the assayable product in the cell indicates its ability to inhibit the activity of the one or more *M. tuberculosis* sigma factors. Test compounds which decrease the activity of the one or more *M. tuberculosis* sigma factors may reactivate latent *M. tuberculosis*. These compounds can be used in the treatment of active tuberculosis to neutralize the one or more *M. tuberculosis* sigma factors and prevent mycobacterial adaptation so that mycobacteria cannot make the changes necessary to evade the host immune system and enter an antibiotic-insensitive latent state. These compounds can also be used in the treatment of latent tuberculosis to neutralize the one or more *M. tuberculosis* sigma factors and force the mycobacteria to reactivate in a controlled fashion so that they may be inhibited and/or killed quickly and efficiently using antibiotics. The compound and the antibiotic can be administered either (a) simultaneously (optionally by formulating the two together in a common carrier), or (b) at different times during the course of a common treatment schedule. In the latter case, the two compounds are administered at times sufficiently close for the antibiotic to efficiently kill or inhibit the growth of the reactivated *M. tuberculosis*. This may be within one month, one week, one day or one hour.

In vitro Screening Assays. The test compounds may be screened in an in vitro assay to identify compounds capable of binding the protein complexes or interacting protein members thereof. For this purpose, a test compound is contacted with a protein complex or an interacting protein member thereof under conditions and for a time sufficient to allow specific interaction between the test compound and the target components to occur, thereby resulting in the binding of the compound to the target, and the formation of a complex. Subsequently, the binding event is detected.

Various screening techniques known in the art may be used. The protein complexes and the interacting protein members thereof may be prepared by any suitable methods, e.g., by recombinant expression and purification. The protein complexes and/or interacting protein members thereof (both are referred to as "target" hereinafter in this section) may be free in solution. A test compound may be mixed with a target forming a liquid mixture. The compound may be labeled with a detectable marker. Upon mixing under suitable conditions, the binding complex having the compound and the target may be co-immunoprecipitated and washed. The compound in the precipitated complex may be detected based on the marker on the compound.

In one embodiment, the target is immobilized on a solid support or on a cell surface. The target can be arrayed into a protein microchip in a method described above. For example, a target may be immobilized directly onto a microchip substrate such as glass slides or onto multi-well plates using non-neutralizing antibodies, i.e., antibodies capable of binding to the target but do not substantially affect its biological activities. To affect the screening, test compounds can be contacted with the immobilized target to allow binding to occur to form complexes under standard binding assay conditions. Either the targets or test compounds are labeled with a detectable marker using well-known labeling techniques. To identify binding compounds, one may measure the formation of the target-test compound complexes or kinetics for the formation thereof.

Alternatively, the test compounds can be immobilized on a solid support, e.g., forming a microarray of test compounds. The target protein or protein complex is then contacted with the test compounds. The target may be labeled with any suitable detection marker. For example, the target may be labeled with radioactive isotopes or fluorescence marker before binding reaction occurs. Alternatively, after the binding reactions, antibodies that are immunoreactive with the target and are labeled with radioactive materials, fluorescence markers, enzymes, or labeled secondary anti-Ig antibodies may be used to detect any bound target thus identifying the binding compound. One example of this embodiment is the protein probing method. That is, the target is used as a probe to screen expression libraries of proteins or random peptides. The expression libraries can be phage display libraries, in vitro translation-based libraries, or ordinary expression cDNA libraries. The libraries may be immobilized on a solid support such as nitrocellulose filters. The probe may be labeled with a radioactive isotope or a fluorescence marker. Alternatively, the probe can be biotinylated and detected with a streptavidin-alkaline phosphatase conjugate. More conveniently, the bound probe may be detected with an antibody.

Test compounds may also be screened in an in vitro assay to identify compounds capable of dissociating the protein complexes. Thus, for example, any one of the interacting pairs of proteins described in the tables above can be contacted with a test compound and the integrity of the protein complex can be assessed. Conversely, test compounds may also be screened to identify compounds capable of enhancing the interactions between the constituent members of the protein complexes formed by the interactions described in the tables. The assays can be conducted in a manner similar to the binding assays described above. For example, the presence or absence of a particular pair of interacting proteins can be detected by an antibody selectively immunoreactive with the protein complex formed by those two proteins. Thus, after incubation of the protein complex with a test compound, an immunoprecipitation assay can be conducted with the antibody. If the test compound disrupts the protein complex, then the amount of immunoprecipitated protein complex in this assay will be significantly less than that in a control assay in which the same protein complex is not contacted with the test compound. Similarly, two proteins—the interaction between which is to be enhanced—may be incubated together with a test compound. Thereafter, a protein complex formed by the two interacting proteins may be detected by the selectively immunoreactive antibody. The amount of protein complex may be compared to that formed in the absence of the test compound. Various other detection methods may be suitable in the dissociation assay, as will be apparent to a skilled artisan.

In another embodiment, fluorescent resonance energy transfer (FRET) is used to screen for modulators of interacting proteins of the protein complexes. FRET assays measure the energy transfer of a fluorescent label to another fluorescent label. Fluorescent labels absorb light preferentially at one wavelength and emit light preferentially at a second wavelength. FRET assays utilize this characteristic by selecting a fluorescent label, called a donor fluorophore, that emits light preferentially at the wavelength a second label, called the acceptor fluorophore, preferentially absorbs light. The proximity of the donor and acceptor fluorophore can be determined by measuring the energy transfer from the donor fluorophore to the acceptor fluorophore. Measuring the energy transfer is performed by shining light on a solution containing acceptor and donor fluorophores at the wavelength the donor fluorophore absorbs light and measuring fluorescence at the wavelength the acceptor fluorophore emits light. The amount of fluorescence of the acceptor fluorophore indicates the proximity of the donor and acceptor fluorophores.

In one embodiment, yeast two-hybrid systems or their analogous or derivative forms is used. Typically, in a classic transcription-based two-hybrid assay, two chimeric genes are prepared encoding two fusion proteins: one contains a transcription activation domain fused to an interacting protein member of a protein complex or an interaction domain or fragment of the interacting protein member, while the other fusion protein includes a DNA binding domain fused to another interacting protein member of the protein complex or a fragment or interaction domain thereof. For the purpose of convenience, the two interacting protein members, fragments or interaction domains thereof are referred to as "bait fusion protein" and "prey fusion protein," respectively. The chimeric genes encoding the fusion proteins are termed "bait chimeric gene" and "prey chimeric gene," respectively. Typically, a "bait vector" and a "prey vector" are provided for the expression of a bait chimeric gene and a prey chimeric gene, respectively.

Generally, the bait and prey vectors include an expression cassette having a promoter operably linked to a chimeric gene for the transcription of the chimeric gene. The vectors may also include an origin of DNA replication for the replication of the vectors in host cells and a replication origin for the amplification of the vectors in, e.g., *E. coli*, and selection marker(s) for selecting and maintaining only those host cells harboring the vectors. Additionally, the expression cassette may also contain inducible elements, which function to control the expression of a chimeric gene. Making the expression of the chimeric genes inducible and controllable is especially important in the event that the fusion proteins or components thereof are toxic to the host cells. Other regulatory sequences such as transcriptional enhancer sequences and translation regulation sequences (e.g., Shine-Dalgarno sequence) can also be included in the expression cassette. Termination sequences such as the bovine growth hormone, SV40, lacZ and AcMNPV polyhedral polyadenylation signals may also be operably linked to a chimeric gene in the expression cassette. An epitope tag coding sequence for detection and/or purification of the fusion proteins can also be operably linked to the chimeric gene in the expression cassette. Examples of useful epitope tags include, but are not limited to, influenza virus hemagglutinin (HA), Simian Virus 5 (V5), polyhistidine (6×His), c-myc, lacZ, GST, and the like. Proteins with polyhistidine tags can be easily detected and/or purified with Ni affinity columns, while specific antibodies to many epitope tags are generally commercially available. The vectors can be introduced into the host cells by any techniques known in the art, e.g., by direct DNA transformation, microinjection, electroporation, viral infection, lipofection, gene gun, and the like. The bait and prey vectors can be maintained in host cells in an extrachromosomal state, i.e., as self-replicating plasmids or viruses. Alternatively, one or both vectors can be integrated into chromosomes of the host cells by conventional techniques such as selection of stable cell lines or site-specific recombination.

The in vivo assays can be conducted in many different host cells, including but not limited to bacteria, yeast cells, plant cells, insect cells, and mammalian cells. A skilled artisan will recognize that the designs of the vectors can vary with the host cells used. In one embodiment, the assay is conducted in prokaryotic cells such as *Escherichia coli, Salmonella, Klebsiella, Pseudomonas, Caulobacter*, and *Rhizobium*.

Screening Assays for Interaction Antagonists. The screening assays described herein are useful for identifying compounds capable of interfering with, disrupting, or dissociating the protein-protein interactions formed between members of the interacting protein pairs, or between mutant and wild type, or mutant and mutant forms of these proteins. Since the protein complexes are associated with the presence or status of tuberculosis in the subject, disruption or dissociation of particular protein-protein interactions may be desirable to treat or ameliorate the tuberculosis, or to alleviate disease symptoms. Alternatively, if the presence or status of tuberculosis is associated with increased expression of any of the proteins, or with expression of a mutant form, or forms, of these proteins, then the tuberculosis may be ameliorated, or symptoms reduced, by weakening or dissociating the interaction between the interacting proteins. Also, if a disease or disorder is associated with a mutant form of an interacting protein that form stronger protein-protein interactions with its protein partner than its wild type counterpart, then the tuberculosis may be treated with a compound that weakens, disrupts or interferes with the interaction between the mutant protein and its interacting partner.

In a screening assay for an interaction antagonist, a first protein, which is a protein selected from any of the protein pairs described in the tables (or a homologue, fragment or derivative thereof), or a mutant form of the first protein (or a homologue, fragment or derivative thereof), and a second protein, which is the interacting partner of the first protein identified in the tables above (or a homologue, fragment or derivative thereof), or a mutant form of the second protein (or a homologue, fragment or derivative thereof), are used as test proteins expressed in the form of fusion proteins as described above for purposes of a two-hybrid assay. The fusion proteins are expressed in a host cell and allowed to interact with each other in the presence of one or more test compounds.

In one embodiment, a counterselectable marker is used as a reporter such that a detectable signal (e.g., appearance of color or fluorescence, or cell survival) is present only when the test compound is capable of interfering with the interaction between the two test proteins. In this respect, the reporters used in various "reverse two-hybrid systems" known in the art may be employed.

Examples of suitable counterselectable reporters useful in a yeast system include the URA3 gene (encoding orotidine-5'-decarboxylase, which converts 5-fluoroorotic acid (5-FOA) to the toxic metabolite 5-fluorouracil), the CANT gene (encoding arginine permease, which transports the toxic arginine analog canavanine into yeast cells), the GAL1 gene (encoding galactokinase, which catalyzes the conversion of 2-deoxygalactose to toxic 2-deoxygalactose-1-phosphate), the LYS2 gene (encoding α-aminoadipate reductase, which renders yeast cells unable to grow on a medium containing α-aminoadipate as the sole nitrogen source), the MET15 gene (encoding O-acetylhomoserine sulfhydrylase, which confers on yeast cells sensitivity to methyl mercury), and the CYH2 gene (encoding L29 ribosomal protein, which confers sensitivity to cycloheximide). In addition, any known cytotoxic agents including cytotoxic proteins such as the diphtheria toxin (DTA) catalytic domain can also be used as counterselectable reporters.

As will be apparent, the screening assay can be applied in a format appropriate for large-scale screening. For example, combinatorial technologies can be employed to construct combinatorial libraries of small organic molecules or small peptides. Such combinatorial libraries of compounds can be applied to the screening assay to isolate specific modulators of particular protein-protein interactions. In the case of random peptide libraries, the random peptides can be co-expressed with the fusion proteins in host cells and assayed in vivo.

The screening assays for identifying compounds capable of modulating protein-protein interactions can also be fine-tuned by various techniques to adjust the thresholds or sensitivity of the positive and negative selections. Mutations can be introduced into the reporter proteins to adjust their activities. The uptake of test compounds by the host cells can also be adjusted. For example, yeast high uptake mutants such as the erg6 mutant strains can facilitate yeast uptake of the test compounds. Likewise, the uptake of the selection compounds such as 5-FOA, 2-deoxygalactose, cycloheximide, α-aminoadipate, and the like can also be fine-tuned.

Generally, a control assay is performed in which the above screening assay is conducted in the absence of the test compound. The result of this assay is then compared with that obtained in the presence of the test compound.

Screening Assays for Interaction Agonists. The screening assays can also be used to identify compounds that trigger or initiate, enhance or stabilize the protein-protein interactions formed between members of the interacting protein pairs disclosed in the tables above, or between combinations of mutant and wild type forms of such proteins, or pairs of mutant proteins. For example, if a pathological state of tuberculosis is associated with the decreased expression of any one of the individual proteins, or one of the protein pairs, then the tuberculosis may be treated by strengthening or stabilizing the interactions between the interacting partner proteins in patients. Alternatively, if a pathological state of tuberculosis is associated with a mutant form, or forms, of the interacting proteins that exhibit weakened or abolished interactions with their binding partner(s), then the disease or disorder may be treated with a compound that initiates or stabilizes the interaction between the mutant form, or forms, of the interacting proteins.

Thus, a screening assay can be performed in the same manner as described above, except that a positively selectable marker is used. For example, a first protein, which is any protein selected from the proteins described in the tables (or a homologue, fragment, or derivative thereof), or a mutant form of the first protein (or a homologue, fragment, or derivative thereof), and a second protein, which is an interacting partner of the first protein (or a homologue, fragment, or derivative thereof), or a mutant form of the second protein (or a homologue, fragment, or derivative thereof), are used as test proteins expressed in the form of fusion proteins as described above for purposes of a two-hybrid assay. The fusion proteins are expressed in host cells and are allowed to interact with each other in the presence of one or more test compounds.

A gene encoding a positively selectable marker such as β-galatosidase may be used as a reporter gene such that when a test compound enables, enhances or strengthens the interaction between a first protein, (or a homologue, fragment, or derivative thereof), or a mutant form of the first protein (or a homologue, fragment, or derivative thereof), and a second protein (or a homologue, fragment, or derivative thereof), or a mutant form of the second (or a homologue, fragment, or derivative thereof), β-galatosidase is expressed. As a result, the compound may be identified based on the appearance of a blue color when the host cells are cultured in a medium containing X-Gal.

Generally, a control assay is performed in which the above screening assay is conducted in the absence of the test compound. The result of this assay is then compared with that obtained in the presence of the test compound.

Compounds can also be selected based on structural models of the target protein or protein complex and/or test compounds. In addition, once an effective compound is identified, structural analogs or mimetics thereof can be produced based on rational drug design with the aim of improving drug efficacy and stability, and reducing side effects. Methods known in the art for rational drug design can be used.

In this respect, structural information on the target protein or protein complex is obtained. Atomic coordinates defining a three-dimensional structure of the target protein or protein complex are obtained. For example, each of the interacting pairs can be expressed and purified. The purified interacting protein pairs are then allowed to interact with each other in vitro under appropriate conditions. Optionally, the interacting protein complex can be stabilized by crosslinking or other techniques. The interacting complex can be studied using various biophysical techniques including, e.g., X-ray crystallography, NMR, computer modeling, mass spectrometry, and the like. Likewise, structural information can also be obtained from protein complexes formed by interacting proteins and a compound that initiates or stabilizes the interaction of the proteins. Methods for obtaining such atomic coordinates by X-ray crystallography, NMR, and the like are known in the art and the application thereof to the target protein or protein complex should be apparent to skilled persons in the art of structural biology.

In addition, understanding of the interaction between the proteins of interest in the presence or absence of a modulator can also be derived by mutagenic analysis using a yeast two-hybrid system or other methods for detecting protein-protein interactions. In this respect, various mutations can be introduced into the interacting proteins and the effect of the mutations on protein-protein interaction examined by a suitable method such as the yeast two-hybrid system.

Based on the information obtained, structural relationships between the interacting proteins, as well as between the identified modulators and the interacting proteins are elucidated. For example, for the identified modulators (i.e., lead compounds), the three-dimensional structure and chemical moieties critical to their modulating effect on the interacting proteins are revealed. Using this information and various techniques known in the art of molecular modeling (i.e., simulated annealing), medicinal chemists can then design analog compounds that might be more effective modulators of the protein-protein interactions. For example, the analog compounds might show more specific or tighter binding to their targets, and thereby might exhibit fewer side effects, or might have more desirable pharmacological characteristics (e.g., greater solubility).

In addition, if the lead compound is a peptide, it can also be analyzed by the alanine scanning technique and/or the two-hybrid assay to determine the domains or residues of the peptide important to its modulating effect on particular protein-protein interactions. The peptide compound can be used as a lead molecule for rational design of small organic molecules or peptide mimetics.

Following the selection of desirable compounds according to the methods disclosed above, the methods further provide for the manufacture of the selected compounds. Compounds found to desirably modulate the interaction between the interacting protein pairs, or to desirably modulate the activity or intracellular levels of their constituent proteins, can be manufactured for further experimental studies, or for therapeutic use.

Therapeutic Applications.

As described above, the interactions between the interacting pairs of proteins suggest that these proteins and/or the protein complexes formed by them may be involved in determining the response of a bacillus to a particular environmental or developmental state. Thus, one may modulate such biological processes or treat tuberculosis by modulating the functions and activities of any of the individual proteins, and/or a protein complex comprising some combination of these proteins. As used herein, modulating a protein, or a protein complex comprising some combination of these proteins means altering (enhancing or reducing) the intracellular concentrations or activities of the proteins or protein complexes, e.g., increasing the concentrations of a particular protein, or a protein complex comprising some combination of these proteins, enhancing or reducing their biological activities, increasing or decreasing their stability, altering their affinity or specificity to certain other biological molecules, etc.

Further provided is a method of treatment of tuberculosis comprising identifying a patient that has a tuberculosis, shows symptoms of having tuberculosis, is predisposed to, or at risk of developing tuberculosis, and treating the tuberculosis by modulating a protein complex including one or more sigma factors and one or more interacting proteins.

Kits

A kit may be used for conducting the diagnostic and screening methods described herein. Typically, the kit should contain, in a carrier or compartmentalized container, reagents useful in any of the above-described embodiments of the diagnosis method. The carrier can be a container or support, in the form of, e.g., bag, box, tube, rack, and is optionally compartmentalized. The carrier may define an enclosed confinement for safety purposes during shipment and storage. In one embodiment, the kit includes an antibody selectively immunoreactive with a protein complex. In addition, antibodies against individual interacting protein members of the protein complexes may also be included. The antibodies may be labeled with a detectable marker such as radioactive isotopes, or enzymatic or fluorescence markers. Alternatively, secondary antibodies such as labeled anti-IgG and the like may be included for detection purposes. Optionally, the kit can include one or more of the protein complexes prepared or purified for comparison purposes. Instructions for using the kit or reagents contained therein are also included in the kit.

EXAMPLES

The present methods and kits, thus generally described, will be understood more readily by reference to the following examples, which are provided by way of illustration and are not intended to be limiting of the present methods and kits. The following is a description of the materials and experimental procedures used in the Examples.

Example 1

ECF σ Factors from *M. Tuberculosis* form Stable Complexes with their Interacting Partners In this Example, the formation of complexes between exemplary σ factors and their cognate anti-σ factors was examined. These complexes were first predicted using standard bioinformatics tools. These include homology-based search tools, wherein the existence of a complex in a homologue suggests the existence of a similar complex in *M. tuberculosis*. Based on computational strategies to predict operons, it was examined if the genes corresponding to these σ-anti-σ factor complexes were likely to be co-transcribed. Another conventional tool is molecular docking of these protein complexes using homology models for these proteins. Conditional co-expression of σ-anti-σ factor complexes was examined using DNA microarray data. Experimentally, the existence of these complexes was identified using protein based pull-down assays. The representative complexes shown here are from recombinant proteins produced by co-expressing these proteins in *E. coli*. The details of the clones that were used to obtain these recombinant σ factors are complied in Table 3.

TABLE 3

Clones used to obtain recombinant σ factors and σ- anti-σ factor complexes

| Protein | Rv number | Expression Vector | Forward Primer (5'-3') | Reverse Primer (5'-3') |
|---|---|---|---|---|
| σ$^A$ | Rv2703 | pETDuet | TTA ATA *TCT AGA* GTG GCA GCG ACC AAA GCA AGC ACG G (SEQ ID NO: 1) | TAT TAA *CAT ATG* TCA GTC CAG GTA GTC GCG CAG (SEQ ID NO: 2) |
| σ$^B$ | Rv2710 | pET15b | CAT ATG *GCT AGC* ATG GCC GAT GCA CCC ACA AGG G (SEQ ID NO: 3) | ATT ATT *CTC GAG* GCT GGC GTA CGA CCG CAG C (SEQ ID NO: 4) |
| σ$^C$ | Rv2069 | pET15b | AAT ATA *GCT AGC* ATG ACC GCG ACG GCA AGC GAC GA (SEQ ID NO: 5) | ATT ATT *CTC GAG* GCC GGT GAG GTC GTC GGG CTC C (SEQ ID NO: 6) |
| σ$^D$ | Rv3414c | pET15b | AAT ATA *GCT AGC* ATG GTC GAT CCG GGA GTT AGC C (SEQ ID NO: 7) | ATT ATT *CTC GAG* CGC ATA GTC ACC TGC CGC AAC A (SEQ ID NO: 8) |
| σ$^E$ | Rv1221 | pETDuet | AAT ATA *GCT AGC* ATG GAA CTC CTC GGC GGA CCC (SEQ ID NO: 9) | TAG CTT *CTC GAG* GCG AAC TGG GTT GAC GTG AAC (SEQ ID NO: 10) |

TABLE 3-continued

Clones used to obtain recombinant σ factors and σ- anti-σ factor complexes

| Protein | Rv number | Expression Vector | Forward Primer (5'-3') | Reverse Primer (5'-3') |
|---|---|---|---|---|
| $\sigma^F$ | Rv3286c | pET15b | AAT ATT CAT ATG GTG ACG GCG CGC GCT GCC GGC GG (SEQ ID NO: 11) | TTA ATA GGA TCC CTA CTC CAA CTG ATC CCG TAG C (SEQ ID NO: 12) |
| $\sigma^G$ | Rv0182c | pET15b | AAA TTA GCT AGC ATG CGC ACA TCG CCG ATG CCC G (SEQ ID NO: 13) | ATT ATT CTC GAG CAG CGA ATC GGG CAG GCC (SEQ ID NO: 14) |
| $\sigma^H$ | Rv3223c | pGex4T1 | CAT ATG GCT AGC ATG GCC GAC ATC GAT GGT GTA (SEQ ID NO: 15) | GTA TAA CTC GAG TCA TGA CGA CAC CCC CTC GTG CGC (SEQ ID NO: 16) |
| $\sigma^I$ | Rv1189 | pET15b | TCGAGCTCGATGTCGCAACACGACCC G (SEQ ID NO: 17) | TAGCGGCCGCCTAACCGCCGCCGAGTTC GGC (SEQ ID NO: 18) |
| $\sigma^J$ | Rv3328c | pET15b | TTA TTA GCT AGC ATG GAG GTT TCC GAA TTC GAG GCA (SEQ ID NO: 19) | TTA AAT CTC GAG ATT CCG GTG ATG CCT GCC GC (SEQ ID NO: 20) |
| $\sigma^K$ | Rv0445c | pETDuet | AAGAGCTCGATGACCGGACCGCCAC GG (SEQ ID NO: 21) | GGCGGCCGCTCATGACACGTCCAGGCAG TT (SEQ ID NO: 22) |
| $\sigma^L$ | Rv0735 | pET15b | GCGGATCCACATATGGTGGCTCGTGT GTCGGGC (SEQ ID NO: 23) | GCAAGCTTCTCGAGTCATCGAGTAACTCC CAGTTC (SEQ ID NO: 24) |
| $\sigma^M$ | Rv3911 | pET15b | AAT ATA GCT AGC ATG CCG CCA CCG ATT GGT TAC T (SEQ ID NO: 25) | ATT ATT CTC GAG TGC CCG GTG GCA ATA GCC AGA TG (SEQ ID NO: 26) |
| PvdS | Rv3232c | pET15b | AAT ATA GCT AGC GTG GAT ATA CCA TCC GTT GAT GT (SEQ ID NO: 27) | ATT ATT CTC GAG CCG GGC GAT CAA CGT GGC C (SEQ ID NO: 28) |

The protein complexes were separated by SDS-PAGE (FIG. 1). Lane 1 shows the separation of the $\sigma^D$ and anti $\sigma^D$ complex; Lane 2 shows the separation of the $\sigma^E$ and Rv1222 complex; Lane 3 shows the separation of the $\sigma^F$ and RsbW complex; Lane 4 shows the separation of the $\sigma^K$ and Rv0444c complex; and Lane 6 corresponds to the $\sigma^L$ and anti $\sigma^L$ pair. Lane 5 is a molecular weight marker (Sigma-Aldrich, Inc.). The σ factors and anti-σ factors are shown by solid and dashed boxes on the gel, respectively.

Example 2

Interactions Between $\sigma^L$ and RslA in Response to Oxidative Stress

In this Example, the formation of complexes between $\sigma^L$ and RslA in response to oxidative stress was examined. The results of this experiment demonstrate that detection of protein complexes in M. tuberculosis can provide information on how the bacillus maintains a sustained latent phase in the host, despite various levels of oxidative stress. As such, the detection of protein complexes involving one or more sigma factors and one or more interacting proteins is useful in methods for the detection and monitoring of M. tuberculosis infection.

Cloning, expression and purification of different $\sigma^L$ and anti-$\sigma^L$ constructs used in this study. The details of the expression constructs used in this study are compiled in Table 3. After transforming the plasmids into Rosetta(DE3)pLysS cells (Novagen, Inc.), the cells were grown in Luria broth with antibiotics (100 µg/ml ampicillin and 30 µg/ml chloramphenicol) to an $A_{600}$ nm of 0.5-0.6. The cells were induced with 0.5 mM IPTG (final concentration). Subsequently, the growth temperature was lowered to 290 K, and cells were grown for further 12-18 h before they were spun down and stored at 193 K. Cells were lysed by sonication in lysis buffer (20 mM Tris pH 7.5 and 250 mM NaCl). The lysate was spun down at ~20000 g to pellet the cell debris. Cell free lysate was incubated with Ni-NTA beads and washed with 10 bed volumes of lysis buffer in the column. The bound protein was eluted by a gradient of elution buffer (20 mM Tris pH 7.5, 250 mM NaCl and 200 mM imidazole). The recombinant proteins were further purified by size exclusion chromatography using a Superdex S-200 column (GE Healthcare) after the affinity chromatography step. The proteins were then concentrated using a membrane based centrifugal ultra filtration system (Amicon-Ultra). The purity of the samples was analyzed by SDS-PAGE with Coomassie Blue staining The molecular weights of the recombinant proteins were verified by mass spectrometry both on a MALDI-TOF as well as LC-ESI-MS (Bruker Daltonics, Inc.) mass spectrometers. The protein concentrations were estimated using UV absorption at 280 nm using the calculated molar extinction coefficients.

TABLE 4

Expression Constructs Used in this Example

| S. No. | Vector | MCS1 | MCS2 |
|---|---|---|---|
| 1 | pET-Duet1 | N-term His-tag Rsl1A 1-108 | $\sigma^L$ 1-177 |
| 2 | pET-Duet1 | N-term His-tag $\sigma^L$ 1-177 | RslA 1-108 |

TABLE 4-continued

Expression Constructs Used in this Example

| S. No. | Vector | MCS1 | MCS2 |
|---|---|---|---|
| 3 | pET-Duet1 | N-term His-tag $\sigma^L$ 1-177 | — |
| 4 | pET-Duet1 | N-term His-tag Rsl1A 1-108 | — |
| 5 | pET-Duet1 | N-term His-tag $\sigma^L$ 1-95 | — |
| 6 | pET-Duet1 | N-term His-tag $\sigma^L$ 100-177 | — |

Preparation of apo and Zinc saturated RslA. Apo RslA was prepared by oxidizing the sample with 1 mM $H_2O_2$ in the presence of 5 mM TPEN (a $Zn^{2+}$ chelator). TPEN and $H_2O_2$ were subsequently removed by gel filtration chromatography using a Superdex S-200 column (Amersham Biosciences). To prepare $Zn^{2+}$ saturated RsrA, purified RsrA was incubated with 1:1 $ZnCl_2$ in 1 mM DTT overnight at 4° C. Unbound $Zn^{2+}$ was removed by several washes of buffer using a centrifugal ultra filtration system (Amicon-Ultra).

Fluorescence Spectroscopy. All fluorescence studies were performed on a JOBIN YVON FlouroMax-3 fluorimeter at room temperature. The fluorescence excitation was set at 280 nm and emission spectra were recorded from 300 to 400 nm at a bandwidth of 1 nm. The excitation and emission slit widths were set to 3 and 5 mm respectively. Each recorded spectrum represents an average of five scans. The spectra were obtained at a protein concentration of 5-10 μM in 5 mM Tris-HCl at pH 7.5 in the presence of 1 mM DTT.

CD spectroscopy. CD experiments were carried out on a JASCO-J715 instrument. All spectra were recorded in 5 mM Tris-HCl buffer adjusted to pH 7.5 with 1 mM DTT using a 1 mm pathlength cuvette. Protein concentrations were kept in the range of 5-15 μM. Each reported spectrum is an average of 5 scans.

PAR assay for Zinc measurements. The metal chelator PAR, when complexed with free $Zn^{2+}$ absorbs light intensively at 500 nm (Bae et al., 1999). The time course of $Zn^{2+}$ release under oxidizing and reducing conditions were measured. Briefly, $Zn^{2+}$ saturated samples were prepared as described earlier. For the assay, protein samples were diluted to 5-10 μM in a buffer containing 0.1 mM PAR. All buffers were purged with $N_2$ gas. Non-specifically bound $Zn^{2+}$ was trapped by PAR in the absence of oxidation, as monitored by a slight increase in absorbance at 500 nm. When absorbance did not increase further, 10 mM $H_2O_2$ was added, and $A_{500}$ was monitored every 30 seconds for 25-50 minutes at 25° C.

Limited proteolysis experiments. Limited proteolysis experiments were carried out at room temperature with 1:2000 protease:protein concentration. The samples were incubated for various time points. For MALDI-TOF experiments reactions were stopped by adding 1% of TFA (final concentration) and for SDS-PAGE analysis reactions were stopped by adding the loading dye solution and boiling the samples for 5 min.

Size exclusion chromatography. For analytical gel filtration experiments, ~0.2-0.3 mg protein samples were run on a Superdex S-200 10/300 GL column equilibrated with 20 mM Tris-HCl (pH 7.5), 200 mM NaCl at 4° C. The peak fractions were collected and analysed on a SDS-PAGE.

Surface Plasmon Resonance Spectroscopy. The kinetics of interaction between RslA and $\sigma^L$ were studied using surface Plasmon resonance (BIACORE 2000, GE Healthcare). RslA was immobilized on a CM5 chip (BIACORE, GE Healthcare) at a surface density of 12 ng/mm². $\sigma^L$, $\sigma^L_2$ and $\sigma^L_4$ at varying concentrations were used as analytes. The first panel of the CM5 chip served as a control. Interaction studies were carried out in 20 mM Tris-HCl buffer (pH 7.8), 200 mM NaCl and 50 mM imidazole. For experiments with apo-RslA, a buffer containing 10 mM $H_2O_2$ and 2 mM TPEN was passed on the chip to remove bound $Zn^{2+}$.

A reducing environment was maintained with 1 mM DTT for interaction studies with holo-RslA, although no substantial changes were noted without DTT. For interaction studies with apo-RslA, a buffer without DTT was used. Binding constants were estimated using the BIA-evaluation software (BIACORE, GE Healthcare).

LC-ESI-MS analysis of RslA. The Cys residues in apo and holo RslA were modified using iodoacetamide which provides a mass difference of 58 Da for each modified Cys. Both apo- and holo-RslA samples were incubated with ~50 fold molar excess of iodoacetamide in 50 mM ammonium bicarbonate (pH 8.0) at 37° C. for 45 min. LC-ESI-MS (Bruker Daltonics, Inc.) was carried out using a C8-analytical column. The mass differences obtained were in the error range of ±2 Da.

Thermal denaturation experiments. Thermal denaturation experiments were carried out on a UV-Visible spectrophotometer (JASCO V-530) at a fixed wavelength of 400 nm in a 10 mm path length quartz cell. The protein concentration used varied from 5-10 JM in 250 mM NaCl and 20 mM sodium phosphate buffer (pH 7.5). The temperature was varied from 20-90° C. at the rate of 1° C. per min.

RslA is a Zinc Binding Antisigma (ZAS) protein. The presence of the $HX_3CX_2C$ sequence motif in Mtb RslA led to its inclusion as a putative member of the ZAS family of proteins. Based on the location of this sequence in the N-terminal cytosolic domain, an expression construct producing recombinant RslA corresponding to the N-terminal domain (1-108) served as a starting point of this study. Recombinant $\sigma^L$, cloned in the pET-Duet expression vector (Novagen, Inc.) was poorly soluble and could not be concentrated beyond ~0.3 mg/ml. However co-expression of Mtb $\sigma^L$ with the N-terminal domain of RslA dramatically improved the expression and solubility of the recombinant proteins and the complex could be concentrated upto ~15 mg/ml. A list of all the expression constructs examined in this study is compiled in Table 3.

Mtb RslA binds $Zn^{2+}$ in a 1:1 stoichiometry. A chromophoric $Zn^{2+}$ specific chelator 4-(2-pyridylazo)-resorcinol (PAR) was used to monitor and quantify the release of $Zn^{2+}$ from RslA and the $\sigma^L$-RslA complex. The PAR assay was performed as described above (procedure adapted from Bae et al., 2004). Monitoring the time course for $Zn^{2+}$ release in the presence of 10 mM $H_2O_2$ showed that the $t_{1/2}$ for the release of bound $Zn^{2+}$ was ~3.5 min (FIG. 2A). Under reducing conditions (in the presence of 1 mM DTT) no release of $Zn^{2+}$ could be detected. Thus RslA, like other ZAS proteins, releases $Zn^{2+}$ under oxidizing conditions. An interesting feature here is the difference in the rate of $Zn^{2+}$ release between Sco RsrA and Mtb RslA. $Zn^{2+}$ is released rapidly upon oxidation of RsrA with a $t_{1/2}$ of ~1.8 min (Bae et al., 2004). The release of bound $Zn^{2+}$ in the $\sigma^L$-RslA complex is far slower than that of RslA alone. The $t_{1/2}$ for $Zn^{2+}$ release in this case is ~5.5 min (FIG. 2A). Removal of bound $Zn^{2+}$ also leads to considerable changes in the secondary structure of RslA and the $\sigma^L$-RslA complex (FIG. 2B). Monitoring the change in the Circular Dichroism spectra (mean residue ellipticity at 222 nm) suggests that the conformational change in the protein occurs at a rate that is substantially slower than $Zn^{2+}$ release. The $t_{1/2}$ for the conformational change upon $Zn^{2+}$ removal monitored using CD spectroscopy is ~7 min for RslA alone while that for the complex is ~12 min. The differences between the rates of $Zn^{2+}$ release and the rate of conformational change thus suggest that while $Zn^{2+}$ release is a rapid response, structural changes provide a much slower second step of the redox sensing mechanism in RslA. $Zn^{2+}$ binding substantially influences the ability of RslA to bind $\sigma_L$. The interaction between $\sigma_L$ and RslA was examined by surface plasmon resonance (SPR) measurements. An analysis of the SPR data suggests that the $\sigma^L$-RslA complex has a dissociation constant ($K_D$) of ~20 nM (FIG. 2C). This binding affinity is comparable to that reported for the Sco $\sigma^R$-RsrA complex (~10 nM) (Kang et al., 1999). $Zn^{2+}$ free RslA (apo RslA) binds $\sigma^L$ with a 7 fold reduced affinity ($K_D$~150 nM), again comparable to the ten fold reduction in binding affinity in the case of Sco $\sigma^R$-RsrA (FIG. 2D). The main differences between these two systems is that in SPR experiments on the $\sigma^L$-RslA complex, we do not observe significant changes in the presence or absence of DTT whereas a significant reduction in affinity was noted in the absence of DTT in the case of Sco $\sigma^R$-RsrA.

Figure 3:
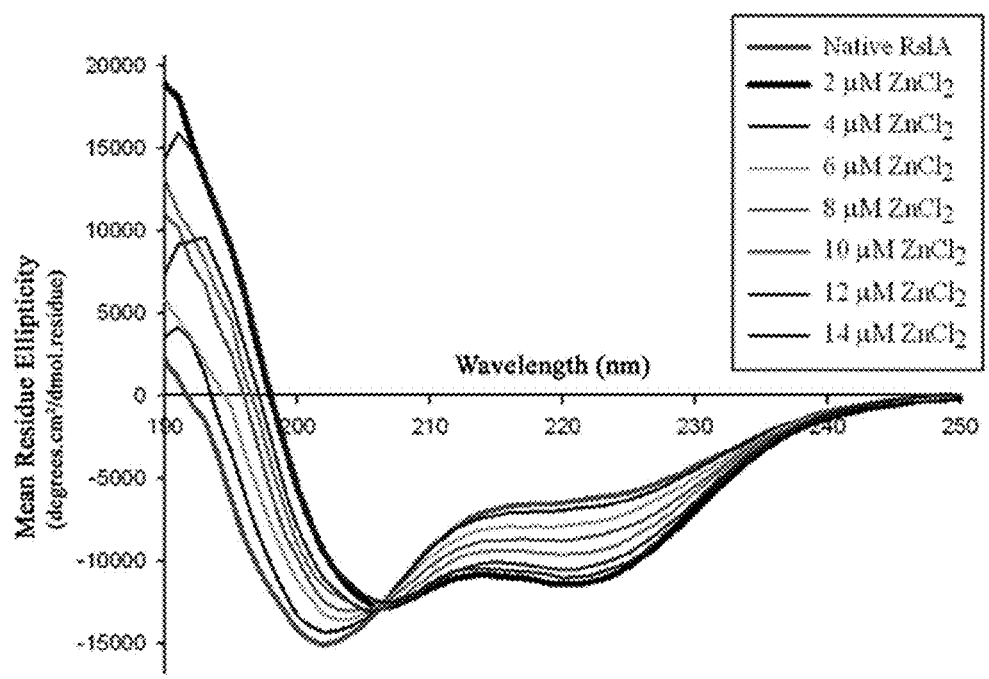
FIG. 3 is a series of graphs showing illustrative embodiments of zinc binding and oxidation-induced conformational changes in RslA and the $\sigma^L$-RslA complex. Panel A is a graph of CD spectra showing changes in secondary structure of RslA induced by increasing concentration of $Zn^{2+}$ under reduced conditions. Panel B is a graph of CD spectra of RslA upon incubation with different metal cofactors.
Figure 3:
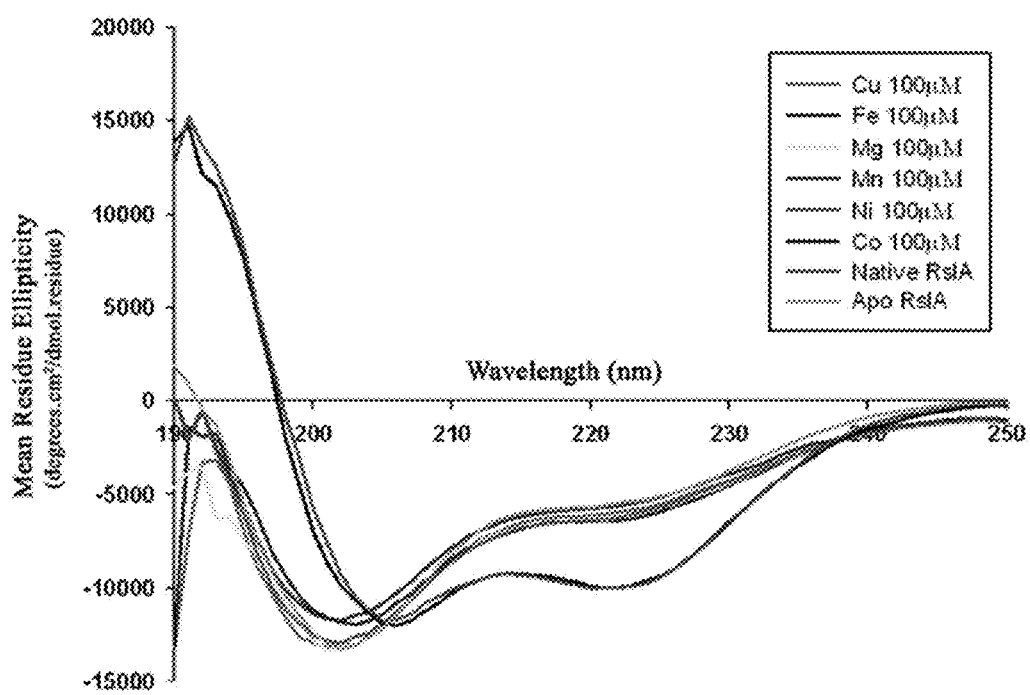

Conformational features of the $\sigma^L$-RslA complex. RslA shows substantial changes in its secondary structural composition upon binding $Zn^{2+}$. The conformational differences between apo and holo RslA were monitored by far UV Circular Dichroism spectroscopy (FIG. 3A). A titration with $Zn^{2+}$ showed a consistent change in the CD spectrum of RslA with increasing $Zn^{2+}$ concentration. When the $Zn^{2+}$ concentration reached stoichiometric concentrations, no further change in the spectrum of RslA was observed. These results are consistent with the inferences from the fluorescence spectroscopy experiments (data not shown). The preference for $Zn^{2+}$ as a metal co-factor is evident from the changes in the CD spectra when RslA was incubated with other metal ions. Amongst the other metal ions that we analyzed viz., $Mg^{2+}$, $Mn^{2+}$, $Cu^{2+}$, $Fe^{2+}$, $Ni^{2+}$ and $Co^{2+}$, none, with the exception of $Co^{2+}$, could replicate the CD spectrum of $Zn^{2+}$ bound RslA (FIG. 3B). This was only possible when $Co^{2+}$ was present at a ten fold molar excess concentration as compared to $Zn^{2+}$.

Figure 4:
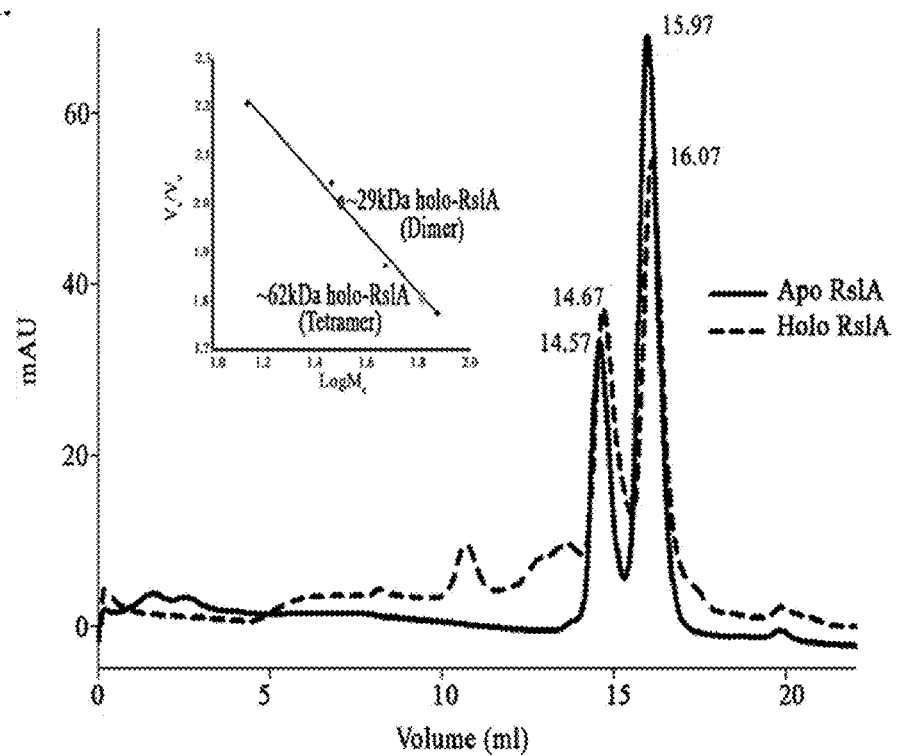
FIG. 4 presents data showing illustrative embodiments of the conformational features of the $\sigma^L$-RslA complex. Panel A shows an analytical size exclusion profile of apo- and holo-RslA. Panel B shows a limited proteolysis experiment of $\sigma^L$-RslA complex. This complex was incubated with trypsin and SDS-PAGE was run to analyze the samples removed at various time points: Lane 1, 0 min; Lane 2, 5 min; Lane 3, 10 min; Lane 4, 20 min; Lane 5, 30 min and Lane 6, 60 min. Panel C shows MALDI-TOF analysis of proteolyzed samples at various time intervals. Based on the molecular weight of corresponding peaks (i, ii, iii, iv) in the MALDI-TOF spectrum (lower panel) $\sigma^L_2$ and $\sigma^L_4$ of $\sigma^L$ were mapped on to the $\sigma^L$ sequence (upper panel).
Figure 4:
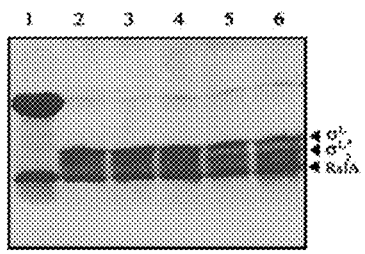
Figure 4:
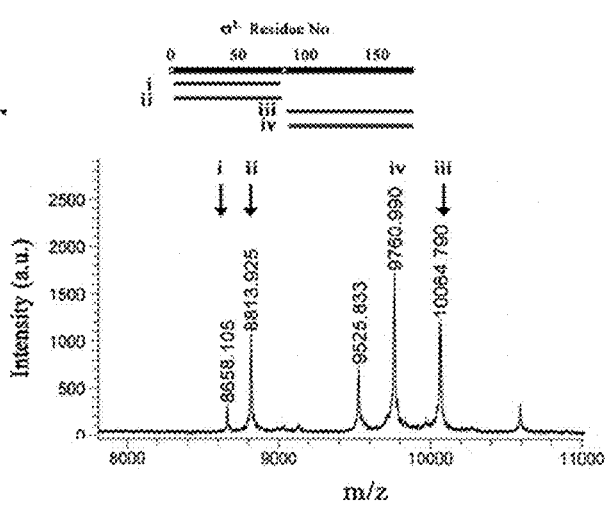
Figure 5:
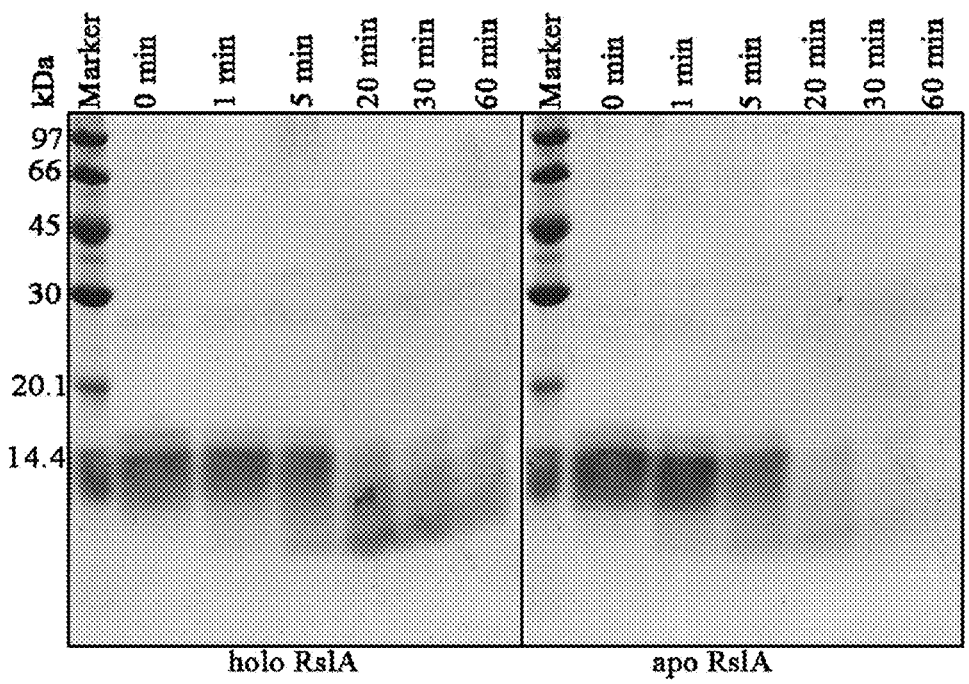
FIG. 5 presents data showing illustrative embodiments of the stability of the *M. tuberculosis* protein complexes. Panel A shows trypsin sensitivity of holo- and apo-RslA. Holo- and apo-RslA (200 µg each) that were treated with trypsin (1:2000) in 100 µl of reaction mix (20 mM Tris-HCl (pH 7.8), 200 mM NaCl) for 0, 1, 5, 20, 30 and 60 minutes at 25° C. At each time-point, a 10 µl aliquot was removed and reaction was stopped by boiling the samples in SDS loading dye and analyzed using 12% SDS-PAGE. Panel B shows temperature-induced denaturation of $\sigma^L$, RslA and the $\sigma^L$-RslA complex. The temperature was scanned between 10° C.-90° C. with dT/dt of 1° C./min.
Figure 5:
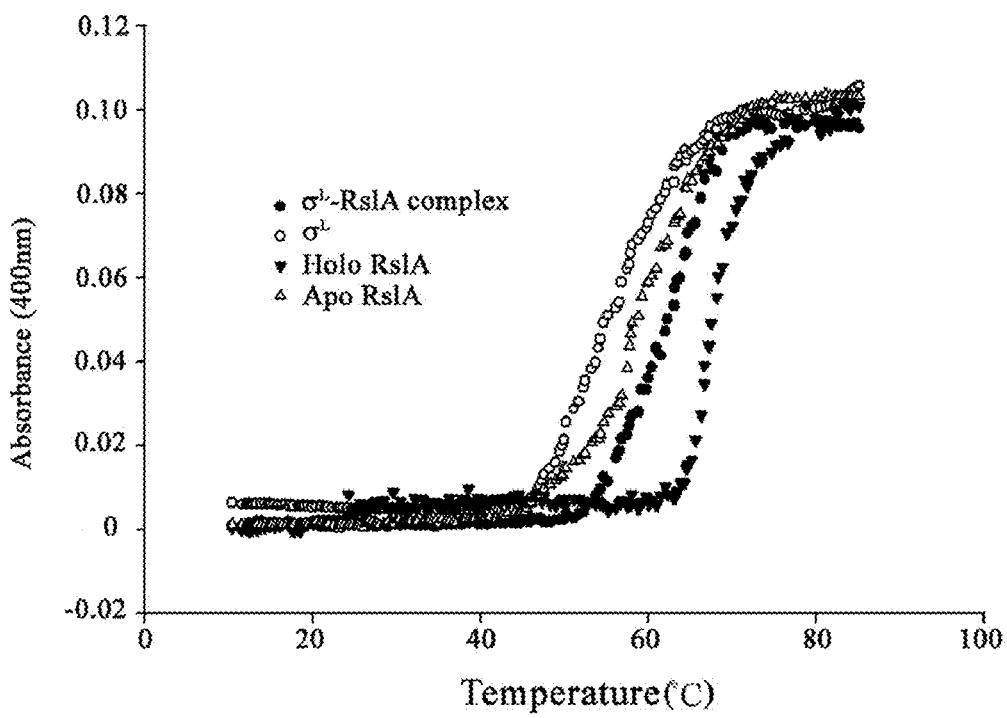

Both apo and holo RslA self associate into dimeric and tetrameric oligomers in solution. This feature was noted by analytical gel filtration experiments (FIG. 4A). This observation is also consistent with data from Dynamic Light Scattering (DLS) measurements (Data not shown). A small shift in the elution profile was observed in the analytical gel filtration experiments between the apo and holo forms, suggesting that $Zn^{2+}$ bound RslA adopts a more compact conformation. The self-association of RslA in solution is similar to the phage λ encoded protein AsiA, that is predominantly a dimer in the free state and differs from Sco RsrA which is a monomer in solution. AsiA, like $\sigma^L$-RslA, forms a 1:1 complex with the *E. coli* primary σ factor $\sigma^{70}$. The AsiA protein is however different from all other characterized σ-anti-σ complexes in that it can exist as a ternary complex with $\sigma^{70}$ and the RNA Polymerase enzyme. The $\sigma^L$-RslA complex was further examined by controlled proteolysis using trypsin. As expected, the two promoter recognition domains $\sigma^L_2$ and $\sigma^L_4$ are the first polypeptide fragments to separate due to the proteolysis of the flexible linker between these segments (FIG. 4B). These two domain segments were unambiguously identified using MALDI-TOF spectrometry (FIG. 4C). The time course measurements suggest that the linker region gets cleaved within a minute of setting up the reaction, even though trypsin concentration was ca. 2000 fold less as compared to the complex. An important observation from this experiment is that RslA remains protected from proteolysis upon complex formation. RslA alone, however, is very susceptible to proteolysis (FIG. 5A). In an effort to identify the relative contributions of the two domains of $\sigma^L$ in complex formation, the interactions of the two domains with RslA were monitored by SPR. $\sigma^L_4$ alone does not interact with RslA (Data not shown). $\sigma^L_2$, on the other hand, binds RslA albeit with a ~100 fold reduction in its affinity as compared to intact $\sigma^L$ ($K_D$~2 μM). This observation is thus similar to that of the Sco $\sigma^R$-RsrA complex, where $\sigma^R_2$ plays a major role in binding RsrA.

Zinc binding confers stability to the $\sigma^L$-RslA complex. RslA is a stable protein with a melting temperature (Tm) of 70° C. $Zn^{2+}$ binding appears to confer thermo-stability to this protein as apo RslA has a Tm of 60° C. Free $\sigma^L$ has a Tm of 56° C. whereas the $\sigma^L$-RslA complex has Tm of 61° C. These data suggest that RslA binding stabilizes $\sigma^L$. Another feature that we note here is that the thermal denaturation shows a single step transition thereby suggesting that the dissociation of the complex and unfolding of these proteins occur simultaneously (FIG. 5B).

Figure 6:
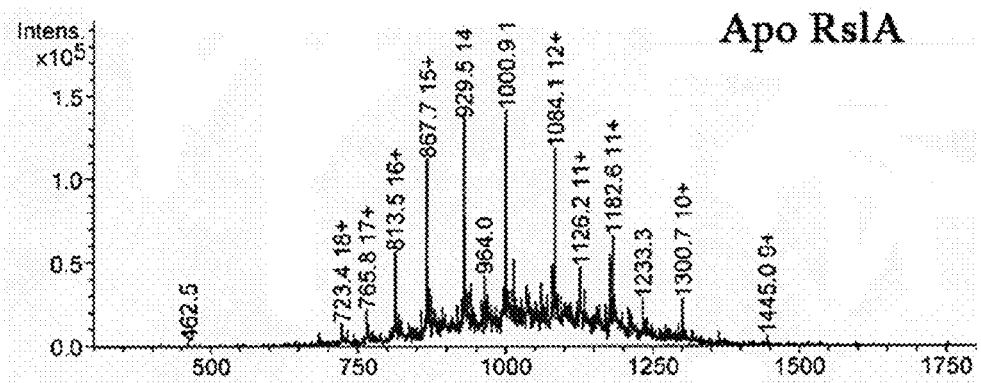
FIG. 6 presents data showing illustrative embodiments that oxidation involves the formation of a disulfide bond in RslA. Panel A is a LC-ESI-MS spectra showing mass differences obtained for oxidized apo-RslA after modification of the Cys residues with iodoacetamide. Panel B is a mass spectrum of reduced, metal bound RslA after modification with iodoacetamide.
Figure 6:
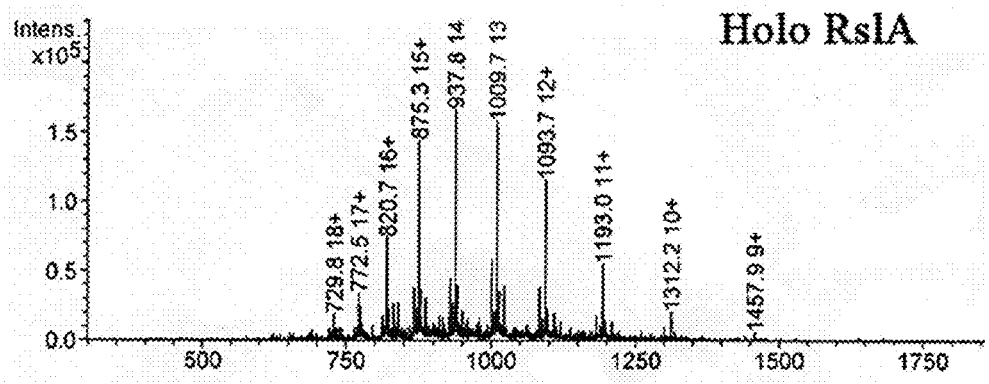

The redox sensor in $\sigma^L$-RslA. The oxidative stress response mechanism of RslA involves disulfide bond formation along with the release of the bound $Zn^{2+}$ cofactor. Based on iodoacetamide labeling of cysteines in holo- and apo-RslA and subsequent analysis by LC-ESI-Mass Spectrometry (ESI-MS), we note that oxidized RslA has one disulfide bond while there are three free cysteines in holo RslA. The expected mass for RslA with all three cysteines modified with iodoacetamide is 13116.5 Da (FIG. 6B). The experimentally determined mass for iodoactetamide treated holo-RslA is 13114.75 Da which is within 2 Da of the calculated mass. The oxidized, disulphide bonded RslA with one Cys residue modified by iodoacetamide has a theoretical mass of 13000.39 Da that also compares well with the experimentally determined mass of 12999.84 Da (FIG. 6A).

Figure 2:
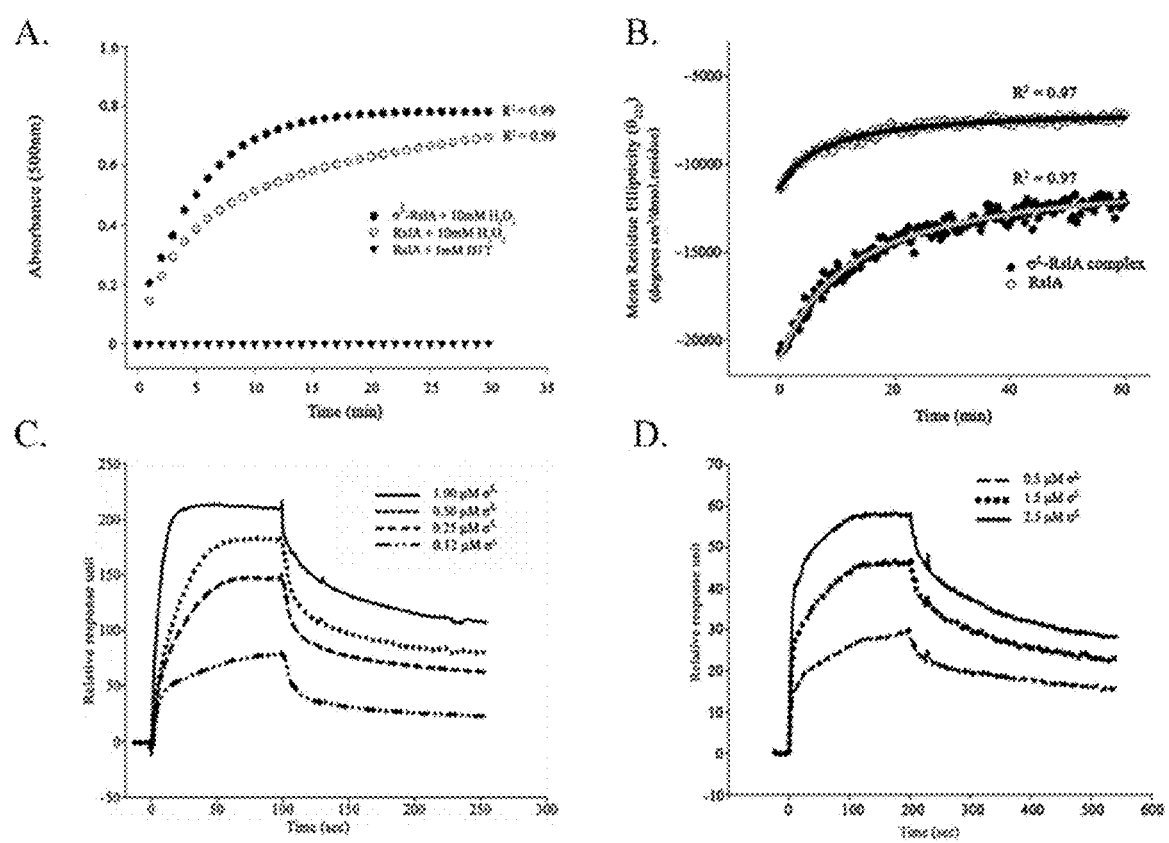
FIG. 2 is a series of graphs showing illustrative embodiments that demonstrate that zinc binding to RslA occurs in reducing conditions. Panel A shows $Zn^{2+}$ release monitored by PAR fluorescence. Panel B shows structural changes in RslA and the $\sigma^L$-RslA complex monitored using CD. Panel C shows surface plasmon resonance studies of $\sigma^L$-RslA interactions. Panel D shows interactions of apo-RslA with $\sigma^L$.

The coordination of $Zn^{2+}$ in the ZAS family of proteins has functional repercussions (FIG. 2). In the case of the other characterized ZAS, RsrA, site-directed mutagenesis analysis where the putative $Zn^{2+}$ coordinating protein ligands were selectively mutated to Ala, led to the finding that the $HX_3CX_2C$ motif was only partially involved in the $Zn^{2+}$ binding. Based on the ability of the Ala mutants to bind $Zn^{2+}$, the putative $Zn^{2+}$ coordinating residues were suggested to be $C^3X_3H_7X_{33}C^{41}X_2C^{44}$, the last four residues were part of the original $HX_3CX_2C$. $Zn^{2+}$ coordination in RsrA was thus proposed to be more similar to the Zinc finger motif proteins (Paget et al., *Mol Microbiol* 39: 1036-47, 2001; Bae et al., *J. Mol. Biol.* 335: 425-35, 2004; Zdanowski et al., *Biochemistry* 45: 8294-300, 2006). An important observation on the Sco $\sigma^R$-RsrA complex was that despite some overlap, residues involved in $Zn^{2+}$ binding and $\sigma^R$ interactions did not necessarily coincide. In the case of Rsp ChrR, the distal Cys residue was replaced by a Histidine. Mtb RslA is similar to Rsp ChrR in $Zn^{2+}$ coordination by virtue of a His in place of the coordinating Cys. ChrR does not respond to oxidative stress; instead it acts as a sensor for a reactive oxygen species (Campbell et al., *Mol cell* 27(5): 793-805, 2007). This finding led to a model whereby a change in the coordination of $Zn^{2+}$ could be correlated to a change in stress detection (oxidative stress in Sco RsrA, singlet oxygen in Rsp ChrR). However, Mtb RslA, unlike ChrR, responds to oxidative stress. The differences between these systems is thus likely to lie in the number of free cysteines, apart from the conserved $HX_3CX_2C$ motif. Mtb RslA has one free Cys (as compared to three in Sco RsrA, none in Rsp ChrR, one in Mtb RseA and four in Mtb RshA). Indeed disulphide bond formation upon oxidation in Sco RsrA, involves cysteines other than the proximal ones in the $HX_3CX_2C$ motif (Bae et al.; *J. Mol. Biol.* 335: 425-35, 2004).

Discussion. ECF σ factors, also referred to as type IV σ factors, are major components of the cellular machinery that synchronize changes in transcription with environmental conditions. The diversity of signals that these proteins respond to include periplasmic stress in gram-negative bacteria, oxidative or disulfide stress, changes in light intensity or resistance to Cobalt or Nickel. An interesting feature of this system is despite the lack of any obvious sequence similarity between either of the two interacting components, the structures of the ECF σ factors and the interacting domain of the anti-σ factor (also referred to as anti-σ domains, ASD) are remarkably well conserved.

Figure 7:
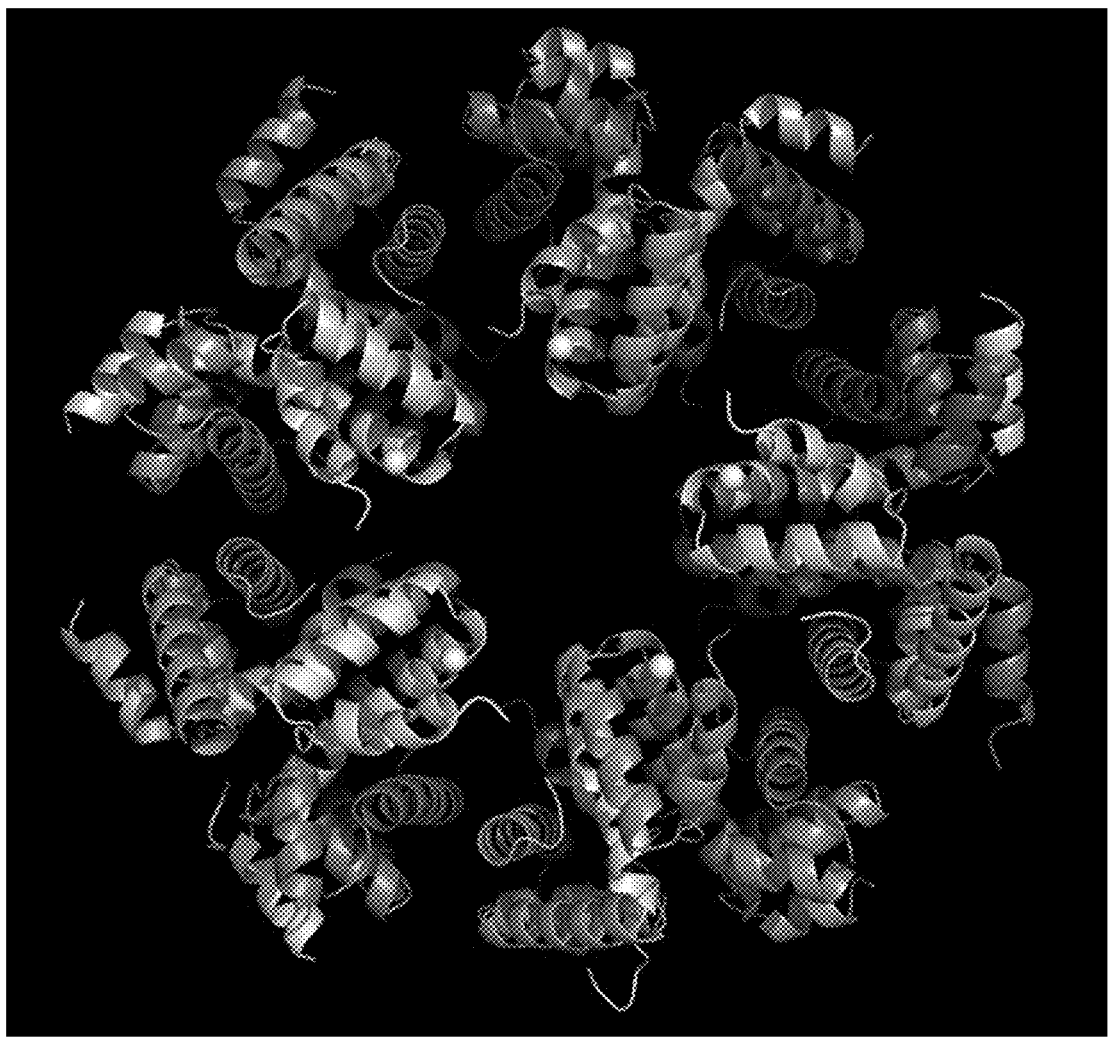
FIG. 7 is a schematic diagram of a model of the crystal structure of the $\sigma^L_4$-RslA complex as determined by Single wavelength Anomalous Dispersion (SAD) with the bound Zinc as the anomalous scatterer. There are ten molecules of this complex in the asymmetric unit of the crystal.

The crystal structure of the $\sigma^L$-RslA complex reveals that only the $\sigma^L_4$ domain remains firmly bound to RslA. It is likely that the $\sigma^L_2$ domain was proteolytically removed in situ after the protein complex was set up for crystallization (FIG. 7). The $\sigma^L$-RslA interaction suggests a model that combines features of several characterized ECF σ factors-anti σ complexes, exemplified by Sco $\sigma^R$-RsrA and Rsp $\sigma^E$-ChrR, as well as features of the principal E. coli σ factor $\sigma^4$-AsiA complex. In the case of the $\sigma^E$-ChrR and the $\sigma^4$-AsiA complexes, the C-terminal domain ($\sigma_4$) of the σ factor appears more prone to structural changes upon complex formation. The commonality here lies in the rearrangement of the HTH motif to abrogate DNA recognition. The $\sigma^E$-ChrR structure shows conformational changes in the region 4, brought about by the unfolding of the terminal helix in region 4.2 (Campbell et al., Mol Cell 27: 793-805, 2007). The $\sigma^4$-AsiA complex, on the other hand, reveals the disruption of the Helix-turn-helix (HTH) motif into a long helical segment (Lambert et al., 2004). The data from the SPR studies, however suggests that substantial involvement of $\sigma^L_4$ is unlikely in Mtb $\sigma^L$-RslA interaction. $\sigma^L_4$ does not interact with either apo or holo RslA, whereas $\sigma^L_2$ does, albeit with substantially lower affinity than the intact protein. Mtb $\sigma^L$-RslA is thus more similar to Sco $\sigma^R$-RsrA (FIG. 7). Thus, while RslA alone is more similar to AsiA based on its propensity to self-associate, the $\sigma^L$-RslA complex is more in agreement with the canonical model for type IV σ-anti σ complexes (Helmann, Adv Microb Physiol 46: 47-110, 2002).

An NADPH dependent thioredoxin reductase reduces thioredoxin. Reduction of glutaredoxin oxidizes the Cys containing tripeptide glutathione, which in turn is reduced by an NADPH-dependent glutathione reductase. The delayed response of Mtb RslA when compared to Sco RsrA, along with the profile of genes directly regulated by Mtb RslA prompts us to speculate that Mtb RslA provides an adaptive mechanism that is triggered upon a sustained oxidative signal. The Mtb $\sigma^L$-RslA system thus provides an additional oxidative response mechanism along with the more immediate regulators governed by Mtb $\sigma^E$ and $\sigma^H$.

To summarize, RslA appears to be a slow response regulator that reacts to sustained oxidative stress. This mechanism appears to be a variant to the repertoire of known ZAS protein responses. Notably, while Sco $\sigma^R$ is activated by superoxide, hydrogen peroxide or diamide in vitro, Rsp $\sigma^E$ does not appear to be affected by these compounds (Kang et al., EMBO J 18: 4292-8, 1999; Anthony et al., J Mol Biol 341: 345-60, 2004). The solution characteristics of the Mtb $\sigma^L$-RslA complex suggest that this module is likely to function more as an adaptive mechanism to oxidative stress rather than a reflex system involved in maintaining a reducing environment in the cytoplasm. This inference is compatible with the regulons governed by $\sigma^L$ that are involved in cell wall and polyketide synthesis as opposed to expression of genes in the thioredoxin cluster as seen in the case of M. tuberculosis $\sigma^E$ and $\sigma^H$. These findings suggest that the signal transduction-transcription relay responds to varied levels of oxidative stress and helps in the sustained latent phase in the host macrophage. As such, the detection of protein complexes involving one or more sigma factors and one or more interacting proteins is useful in methods for the detection and monitoring of M. tuberculosis infection.

EQUIVALENTS

While certain embodiments have been illustrated and described, it should be understood that changes and modifications can be made therein in accordance with ordinary skill in the art without departing from the technology in its broader aspects as defined in the following claims.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

What is claimed is:

1. A method for monitoring tuberculosis in a subject comprising:
    detecting in a sample from the subject
    whether sigma factor $\sigma^L$ of *Mycobacterium tuberculosis* is bound to the $\sigma^L$-interacting protein RslA, wherein the presence of unbound $\sigma^L$ is an indicator of active *Mycobacterium tuberculosis* infection.

2. The method of claim 1, wherein the status of tuberculosis is active tuberculosis, latent infection or recent infection.

3. The method of claim 1, wherein the detecting comprises contacting the sample with a solid support conjugated to one or more binding agents having specific binding sites for sigma factor $\sigma^L$ and detecting whether RslA is bound to the sigma factor $\sigma^L$.

4. The method of claim 3, wherein the solid support is an antibody array.

5. The method of claim 3, wherein the one or more binding agents comprise antibodies that have been raised against sigma factor $\sigma^L$ from *Mycobacterium tuberculosis*.

6. The method of claim 5, wherein the antibodies are polyclonal antibodies.

7. The method of claim 5, wherein the antibodies are monoclonal antibodies.

8. The method of claim 1, further comprising detecting whether one or more additional sigma factors of *Mycobacterium tuberculosis* are bound to one or more interacting proteins, wherein the one or more additional sigma factors are selected from the group consisting of: $\sigma^A$, $\sigma^B$, $\sigma^C$, $\sigma^D$, $\sigma^E$, $\sigma^F$, $\sigma^G$, $\sigma^H$, $\sigma^I$, $\sigma^J$, $\sigma^K$, $\sigma^M$, and pvdS.

9. The method of claim 1, wherein the detecting comprises contacting the sample with a solid support conjugated to recombinant sigma factor $\sigma^L$ and detecting whether RslA is bound to the recombinant sigma factor $\sigma^L$.

10. The method of claim 9, wherein the solid support is an array of recombinant sigma factor $\sigma^L$.

11. The method of claim 1, wherein the detecting comprises immunoprecipitating the sigma factor $\sigma^L$ in the sample and detecting whether RslA is bound to the sigma factor $\sigma^L$.

12. The method of claim 1, wherein the sample is a fluid or tissue sample containing *Mycobacterium tuberculosis*.

13. The method of claim 1, wherein the sample is from an isolated culture of *Mycobacterium tuberculosis* from a sample previously obtained from the subject.

14. The method of claim 1, wherein the sample is a protein extract from a fluid or tissue sample containing *Mycobacterium tuberculosis*.

* * * * *

UNITED STATES PATENT AND TRADEMARK OFFICE
CERTIFICATE OF CORRECTION

| | | |
|---|---|---|
| PATENT NO. | : 8,058,022 B2 | Page 1 of 2 |
| APPLICATION NO. | : 12/560904 | |
| DATED | : November 15, 2011 | |
| INVENTOR(S) | : Gopal | |

It is certified that error appears in the above-identified patent and that said Letters Patent is hereby corrected as shown below:

On the Title Page, in Item [56], "OTHER PUBLICATIONS", in Column 2, Line 36, delete "Is" and insert -- is --, therefor.

On the Title Page, in Item [56], "OTHER PUBLICATIONS", in Column 2, Line 39, delete "tuberculosis,"Journal" and insert -- tuberculosis," Journal --, therefor.

On the Title Page, in Item [56], "OTHER PUBLICATIONS", in Column 2, Line 42, delete "bibbed" and insert -- bilobed --, therefor.

In the Specification

Column 2, Line 46, delete "etionamide," and insert -- ethionamide, --, therefor.

Column 6, Line 44, delete "cross-linking" and insert -- cross-linking. --, therefor.

Column 7, Line 4, delete "ascities" and insert -- ascites --, therefor.

Column 7, Line 42, delete "ascities" and insert -- ascites --, therefor.

Column 10, in Table 2-continued, under "Environmental Conditions", Line 11, delete "plumbagine." and insert -- plumbagin. --, therefor.

Column 10, Line 62, delete "immunosorbant" and insert -- immunosorbent --, therefor.

Column 24, Line 57, delete "CANT" and insert -- CAN1 --, therefor.

Column 25, Line 63, delete "β-galatosidase" and insert -- β-galactosidase --, therefor.

Signed and Sealed this
Twelfth Day of August, 2014

Michelle K. Lee
*Deputy Director of the United States Patent and Trademark Office*

Column 26, Line 3, delete "β-galatosidase" and insert -- β-galactosidase --, therefor.

Column 31, Line 49, delete "protease:protein" and insert -- protease : protein --, therefor.

Column 34, Line 22, delete "iodoactetamide" and insert -- iodoacetamide --, therefor.

SEQUENCE LISTING

<160> NUMBER OF SEQ ID NOS: 30

<210> SEQ ID NO 1
<211> LENGTH: 37
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 1
ttaatatcta gagtggcagc gaccaaagca agcacgg                              37

<210> SEQ ID NO 2
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tattaacata tgtcagtcca ggtagtcgcg cag                                  33

<210> SEQ ID NO 3
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
catatggcta gcatggccga tgcacccaca aggg                                 34

<210> SEQ ID NO 4
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
attattctcg aggctggcgt acgaccgcag c                                    31

<210> SEQ ID NO 5
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
aatatagcta gcatgaccgc gacggcaagc gacga                                35

<210> SEQ ID NO 6
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
attattctcg aggccggtga ggtcgtcggg ctcc                                 34

<210> SEQ ID NO 7
<211> LENGTH: 34
<212> TYPE: DNA
<213> ORGANISM: Artificial Sequence
<220> FEATURE:
<223> OTHER INFORMATION: Description of Artificial Sequence: Synthetic
```

-continued primer

<400> SEQUENCE: 7
aatatagcta gcatggtcga tccgggagtt agcc                                34

<210> SEQ ID NO 8
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
attattctcg agcgcatagt cacctgccgc aaca                                34

<210> SEQ ID NO 9
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
aatatagcta gcatggaact cctcggcgga ccc                                 33

<210> SEQ ID NO 10
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tagcttctcg aggcgaactg ggttgacgtg aac                                 33

<210> SEQ ID NO 11
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
aatattcata tggtgacggc gcgcgctgcc ggcgg                               35

<210> SEQ ID NO 12
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ttaataggat ccctactcca actgatcccg tagc                                34

<210> SEQ ID NO 13
<211> LENGTH: 34
<212> TYPE: DNA
<213> ORGANISM: Artificial Sequence
<220> FEATURE:
<223> OTHER INFORMATION: Description of Artificial Sequence: Synthetic
      primer -continued

<400> SEQUENCE: 13
aaattagcta gcatgcgcac atcgccgatg cccg                34

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
attattctcg agcagcgaat cgggcaggcc                30

<210> SEQ ID NO 15
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
catatggcta gcatggccga catcgatggt gta                33

<210> SEQ ID NO 16
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gtataactcg agtcatgacg acacccctc gtgcgc                36

<210> SEQ ID NO 17
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
tcgagctcga tgtcgcaaca cgacccg                27

<210> SEQ ID NO 18
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
tagcggccgc ctaaccgccg ccgagttcgg c                31

<210> SEQ ID NO 19
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ttattagcta gcatggaggt ttccgaattc gaggca    36

<210> SEQ ID NO 20
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 20
ttaaatctcg agattccggt gatgcctgcc gc    32

<210> SEQ ID NO 21
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 21
aagagctcga tgaccggacc gccacgg    27

<210> SEQ ID NO 22
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 22
ggcggccgct catgacacgt ccaggcagtt    30

<210> SEQ ID NO 23
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 23
gcggatccac atatggtggc tcgtgtgtcg ggc    33

<210> SEQ ID NO 24
<211> LENGTH: 35
<212> TYPE: DNA
<213> ORGANISM: Artificial Sequence
<220> FEATURE:
<223> OTHER INFORMATION: Description of Artificial Sequence: Synthetic primer

<400> SEQUENCE: 24
gcaagcttct cgagtcatcg agtaactccc agttc    35

<210> SEQ ID NO 25
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 25
aatatagcta gcatgccgcc accgattggt tact    34

```
<210> SEQ ID NO 26
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
attattctcg agtgcccggt ggcaatagcc agatg                              35

<210> SEQ ID NO 27
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
aatatagcta gcgtggatat accatccgtt gatgt                              35

<210> SEQ ID NO 28
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
attattctcg agccgggcga tcaacgtggc c                                  31

<210> SEQ ID NO 29
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 29

His His His His His His
1               5

<210> SEQ ID NO 30
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(4)
<223> OTHER INFORMATION: Any amino acid
<220> FEATURE:
<221> NAME/KEY: MOD_RES
<222> LOCATION: (12)..(44)
<223> OTHER INFORMATION: Any amino acid
<220> FEATURE:
<221> NAME/KEY: MOD_RES
<222> LOCATION: (46)..(47)
<223> OTHER INFORMATION: Any amino acid

<400> SEQUENCE: 30

Cys Xaa Xaa Xaa His His His His His His Xaa Xaa Xaa Xaa Xaa
1               5                   10                  15
```

-continued

```
Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Cys Xaa Xaa Cys
            35                  40                  45
```